United States Patent
Wei

(10) Patent No.: US 10,893,941 B2
(45) Date of Patent: *Jan. 19, 2021

(54) TISSUE FIXATION DEVICES AND METHODS

(71) Applicant: Abbott Cardiovascular Systems, Inc., Santa Clara, CA (US)

(72) Inventor: Michael F. Wei, Redwood City, CA (US)

(73) Assignee: Abbott Cardiovascular Systems, Inc., Santa Clara, CA (US)

(*) Notice: Subject to any disclaimer, the term of this patent is extended or adjusted under 35 U.S.C. 154(b) by 115 days.

This patent is subject to a terminal disclaimer.

(21) Appl. No.: 16/050,445

(22) Filed: Jul. 31, 2018

(65) Prior Publication Data

US 2018/0344460 A1 Dec. 6, 2018

Related U.S. Application Data

(63) Continuation of application No. 14/677,294, filed on Apr. 2, 2015, now Pat. No. 10,524,912.

(51) Int. Cl.
*A61F 2/24* (2006.01)
*A61B 17/122* (2006.01)
(Continued)

(52) U.S. Cl.
CPC .......... *A61F 2/2454* (2013.01); *A61B 17/083* (2013.01); *A61B 17/122* (2013.01);
(Continued)

(58) Field of Classification Search
CPC .... A61F 2/2442; A61F 2/2445; A61F 2/2448; A61F 2/2451; A61F 2/2454;
(Continued)

(56) References Cited

U.S. PATENT DOCUMENTS 2,097,018 A 10/1937 Chamberlain
2,108,206 A 2/1938 Meeker
(Continued)

FOREIGN PATENT DOCUMENTS

CA 2296317 C 1/2009
CN 1142351 A 2/1997
(Continued)

OTHER PUBLICATIONS

Copelan, "How Dr. Oz Kick-Started a Groundbreaking Device for Patients with Heart Failure," Parade (Sep. 26, 2018).
(Continued)

*Primary Examiner* — Katherine H Schwiker
(74) *Attorney, Agent, or Firm* — Baker Botts L.L.P.

(57) ABSTRACT

The present disclosure describes tissue gripping devices, systems, and methods for gripping mitral valve tissue during treatment of a mitral valve and while a tissue fixation device is implanted in the mitral valve. The tissue gripping device includes a flexible member and one or more tissue gripping members coupled to one or more arms of the flexible member. The flexible member is formed from a shape-memory material, such as nitinol, and the tissue gripping member(s) are formed from a material that is more rigid than the shape-memory material. The tissue gripping member(s) are attached to the flexible member by threading or looping suture lines around and/or through the tissue gripping member(s) and the flexible member and/or by applying a cover material to the tissue gripping device to hold the tissue gripping member(s) against the flexible member.

12 Claims, 9 Drawing Sheets

(51) Int. Cl.
*A61B 17/08* (2006.01)
*A61B 17/00* (2006.01)

(52) U.S. Cl.
CPC .......... *A61B 17/1227* (2013.01); *A61F 2/246* (2013.01); *A61B 2017/00243* (2013.01); *A61B 2017/00526* (2013.01); *A61B 2017/00867* (2013.01); *A61B 2017/00964* (2013.01); *A61B 2017/081* (2013.01); *A61F 2220/0016* (2013.01)

(58) Field of Classification Search
CPC .................... A61F 2/2457; A61F 2/246; A61F 2220/0016; A61F 2220/0033; A61F 2220/0075; A61B 17/08; A61B 17/083; A61B 17/085; A61B 17/122; A61B 17/1222; A61B 17/1227; A61B 17/0057; A61B 2017/081; A61B 2017/086; A61B 2017/088; A61B 2017/1225; A61B 2017/0458; A61B 2017/00579; A61B 2017/00592; A61B 2017/00597
See application file for complete search history.

(56) References Cited

U.S. PATENT DOCUMENTS

| | | |
|---|---|---|
| 3,296,668 A | 1/1967 | Aiken |
| 3,378,010 A | 4/1968 | Codling et al. |
| 3,557,780 A | 1/1971 | Sato |
| 3,671,979 A | 6/1972 | Moulopoulos |
| 3,675,639 A | 7/1972 | Cimber |
| 3,874,338 A | 4/1975 | Happel |
| 3,874,388 A | 4/1975 | King et al. |
| 4,007,743 A | 2/1977 | Blake |
| 4,055,861 A | 11/1977 | Carpentier et al. |
| 4,056,854 A | 11/1977 | Boretos et al. |
| 4,064,881 A | 12/1977 | Meredith |
| 4,091,815 A | 5/1978 | Larsen |
| 4,112,951 A | 9/1978 | Hulka et al. |
| 4,235,238 A | 11/1980 | Ogiu et al. |
| 4,297,749 A | 11/1981 | Davis et al. |
| 4,327,736 A | 5/1982 | Inoue |
| 4,340,091 A | 7/1982 | Skelton et al. |
| 4,458,682 A | 7/1984 | Cerwin |
| 4,425,908 A | 11/1984 | Simon |
| 4,484,579 A | 11/1984 | Meno et al. |
| 4,487,205 A | 12/1984 | Di Giovanni et al. |
| 4,498,476 A | 2/1985 | Cerwin et al. |
| 4,510,934 A | 4/1985 | Batra |
| 4,531,522 A | 7/1985 | Bedi et al. |
| 4,578,061 A | 3/1986 | Lemelson |
| 4,641,366 A | 2/1987 | Yokoyama et al. |
| 4,657,024 A | 4/1987 | Coneys |
| 4,686,965 A | 8/1987 | Bonnet et al. |
| 4,693,248 A | 9/1987 | Failla |
| 4,716,886 A | 1/1988 | Schulman et al. |
| 4,777,951 A | 10/1988 | Cribier et al. |
| 4,795,458 A | 1/1989 | Regan |
| 4,809,695 A | 3/1989 | Gwathmey et al. |
| 4,917,089 A | 4/1990 | Sideris |
| 4,930,674 A | 6/1990 | Barak |
| 4,944,295 A | 7/1990 | Gwathmey et al. |
| 4,969,890 A | 11/1990 | Sugita et al. |
| 4,994,077 A | 2/1991 | Dobben |
| 5,002,562 A | 3/1991 | Oberlander |
| 5,015,249 A | 5/1991 | Nakao et al. |
| 5,019,096 A | 5/1991 | Fox, Jr. et al. |
| 5,042,707 A | 8/1991 | Taheri |
| 5,047,041 A | 9/1991 | Samuels |
| 5,049,153 A | 9/1991 | Nakao et al. |
| 5,061,277 A | 10/1991 | Carpentier et al. |
| 5,069,679 A | 12/1991 | Taheri |
| 5,098,440 A | 3/1992 | Hillstead |
| 5,108,368 A | 4/1992 | Hammerslag et al. |
| 5,125,758 A | 6/1992 | DeWan |
| 5,125,895 A | 6/1992 | Buchbinder et al. |
| 5,147,370 A | 9/1992 | McNamara et al. |
| 5,171,252 A | 12/1992 | Friedland |
| 5,171,259 A | 12/1992 | Inoue |
| 5,190,554 A | 3/1993 | Coddington et al. |
| 5,195,968 A | 3/1993 | Lundquist et al. |
| 5,209,756 A | 5/1993 | Seedhom et al. |
| 5,222,963 A | 6/1993 | Brinkerhoff et al. |
| 5,226,429 A | 7/1993 | Kuzmak |
| 5,226,911 A | 7/1993 | Chee et al. |
| 5,234,437 A | 8/1993 | Sepetka |
| 5,242,456 A | 9/1993 | Nash et al. |
| 5,250,071 A | 10/1993 | Palermo |
| 5,251,611 A | 10/1993 | Zehel et al. |
| 5,254,130 A | 10/1993 | Poncet et al. |
| 5,261,916 A | 11/1993 | Engelson |
| 5,271,381 A | 12/1993 | Ailinger et al. |
| 5,271,544 A | 12/1993 | Fox et al. |
| 5,275,578 A | 1/1994 | Adams |
| 5,282,845 A | 2/1994 | Bush et al. |
| 5,304,131 A | 4/1994 | Paskar |
| 5,306,283 A | 4/1994 | Conners |
| 5,306,286 A | 4/1994 | Stack et al. |
| 5,312,415 A | 5/1994 | Palermo |
| 5,314,424 A | 5/1994 | Nicholas |
| 5,318,525 A | 6/1994 | West et al. |
| 5,320,632 A | 6/1994 | Heidmueller |
| 5,325,845 A | 7/1994 | Adair |
| 5,327,905 A | 7/1994 | Avitall |
| 5,330,442 A | 7/1994 | Green et al. |
| 5,330,501 A | 7/1994 | Tovey et al. |
| 5,332,402 A | 7/1994 | Teitelbaum |
| 5,334,217 A | 8/1994 | Das |
| 5,342,393 A | 8/1994 | Stack |
| 5,350,397 A | 9/1994 | Palermo et al. |
| 5,350,399 A | 9/1994 | Erlebacher et al. |
| 5,359,994 A | 11/1994 | Kreuter et al. |
| 5,363,861 A | 11/1994 | Edwards et al. |
| 5,368,564 A | 11/1994 | Savage |
| 5,368,601 A | 11/1994 | Sauer et al. |
| 5,383,886 A | 1/1995 | Kensey et al. |
| 5,389,077 A | 2/1995 | Melinyshyn et al. |
| 5,391,182 A | 2/1995 | Chin |
| 5,403,312 A | 4/1995 | Yates et al. |
| 5,403,326 A | 4/1995 | Harrison et al. |
| 5,411,552 A | 5/1995 | Andersen et al. |
| 5,413,584 A | 5/1995 | Schulze |
| 5,417,699 A | 5/1995 | Klein et al. |
| 5,417,700 A | 5/1995 | Egan |
| 5,423,857 A | 6/1995 | Rosenman et al. |
| 5,423,858 A | 6/1995 | Bolanos et al. |
| 5,423,882 A | 6/1995 | Jackman et al. |
| 5,425,744 A | 6/1995 | Fagan et al. |
| 5,431,666 A | 7/1995 | Sauer et al. |
| 5,437,551 A | 8/1995 | Chalifoux |
| 5,437,681 A | 8/1995 | Meade et al. |
| 5,447,966 A | 9/1995 | Hermes et al. |
| 5,450,860 A | 9/1995 | O'Connor |
| 5,452,837 A | 9/1995 | Williamson, IV et al. |
| 5,456,400 A | 10/1995 | Shichman et al. |
| 5,456,674 A | 10/1995 | Bos et al. |
| 5,456,684 A | 10/1995 | Schmidt et al. |
| 5,462,527 A | 10/1995 | Stevens-Wright et al. |
| 5,472,044 A | 12/1995 | Hall et al. |
| 5,476,470 A | 12/1995 | Fitzgibbons, Jr. |
| 5,477,856 A | 12/1995 | Lundquist |
| 5,478,309 A | 12/1995 | Sweezer et al. |
| 5,478,353 A | 12/1995 | Yoon |
| 5,487,746 A | 1/1996 | Yu et al. |
| 5,496,332 A | 3/1996 | Sierra et al. |
| 5,507,725 A | 4/1996 | Savage et al. |
| 5,507,755 A | 4/1996 | Gresl et al. |
| 5,507,757 A | 4/1996 | Sauer et al. |
| 5,520,701 A | 5/1996 | Lerch |
| 5,522,873 A | 6/1996 | Jackman et al. |
| 5,527,313 A | 6/1996 | Scott et al. |
| 5,527,321 A | 6/1996 | Hinchliffe |
| 5,527,322 A | 6/1996 | Klein et al. |

(56) References Cited

U.S. PATENT DOCUMENTS

| | | |
|---|---|---|
| 5,536,251 A | 7/1996 | Evard et al. |
| 5,540,705 A | 7/1996 | Meade et al. |
| 5,542,949 A | 8/1996 | Yoon |
| 5,554,185 A | 9/1996 | Block et al. |
| 5,562,678 A | 10/1996 | Booker |
| 5,569,274 A | 10/1996 | Rapacki et al. |
| 5,571,085 A | 11/1996 | Accisano, III |
| 5,571,137 A | 11/1996 | Marlow et al. |
| 5,571,215 A | 11/1996 | Sterman et al. |
| 5,575,802 A | 11/1996 | McQuilkin et al. |
| 5,582,611 A | 12/1996 | Tsuruta et al. |
| 5,593,424 A | 1/1997 | Northrup, III |
| 5,593,435 A | 1/1997 | Carpentier et al. |
| 5,601,224 A | 2/1997 | Bishop et al. |
| 5,601,574 A | 2/1997 | Stefanchik et al. |
| 5,607,462 A | 3/1997 | Imran |
| 5,607,471 A | 3/1997 | Seguin et al. |
| 5,609,598 A | 3/1997 | Laufer et al. |
| 5,611,794 A | 3/1997 | Sauer et al. |
| 5,618,306 A | 4/1997 | Roth et al. |
| 5,620,452 A | 4/1997 | Yoon |
| 5,620,461 A | 4/1997 | Muijs Van De Moer et al. |
| 5,626,588 A | 5/1997 | Sauer et al. |
| 5,634,932 A | 6/1997 | Schmidt |
| 5,636,634 A | 6/1997 | Kordis et al. |
| 5,639,277 A | 6/1997 | Mariant et al. |
| 5,640,955 A | 6/1997 | Ockuly et al. |
| 5,649,937 A | 7/1997 | Bito et al. |
| 5,662,681 A | 9/1997 | Nash et al. |
| 5,669,917 A | 9/1997 | Sauer et al. |
| 5,690,671 A | 11/1997 | McGurk et al. |
| 5,695,504 A | 12/1997 | Gifford, III et al. |
| 5,695,505 A | 12/1997 | Yoon |
| 5,702,825 A | 12/1997 | Keital et al. |
| 5,706,824 A | 1/1998 | Whittier |
| 5,709,707 A | 1/1998 | Lock et al. |
| 5,713,910 A | 2/1998 | Gordon et al. |
| 5,713,911 A | 2/1998 | Racene et al. |
| 5,715,817 A | 2/1998 | Stevens-Wright et al. |
| 5,716,367 A | 2/1998 | Koike et al. |
| 5,716,417 A | 2/1998 | Girard et al. |
| 5,718,725 A | 2/1998 | Sterman et al. |
| 5,719,725 A | 2/1998 | Nakao |
| 5,722,421 A | 3/1998 | Francese et al. |
| 5,725,542 A | 3/1998 | Yoon |
| 5,725,556 A | 3/1998 | Moser et al. |
| 5,738,649 A | 4/1998 | Macoviak |
| 5,741,280 A | 4/1998 | Fleenor |
| 5,741,297 A | 4/1998 | Simon |
| 5,749,828 A | 5/1998 | Solomon et al. |
| 5,755,778 A | 5/1998 | Kleshinski |
| 5,759,193 A | 6/1998 | Burbank et al. |
| 5,769,812 A | 6/1998 | Stevens et al. |
| 5,769,863 A | 6/1998 | Garrison |
| 5,772,578 A | 6/1998 | Heimberger et al. |
| 5,782,239 A | 7/1998 | Webster, Jr. |
| 5,782,845 A | 7/1998 | Shewchuk |
| 5,797,927 A | 8/1998 | Yoon |
| 5,797,960 A | 8/1998 | Stevens et al. |
| 5,810,847 A | 9/1998 | Laufer et al. |
| 5,810,849 A | 9/1998 | Kontos |
| 5,810,853 A | 9/1998 | Yoon |
| 5,810,876 A | 9/1998 | Kelleher |
| 5,814,029 A | 9/1998 | Hassett |
| 5,814,097 A | 9/1998 | Sterman et al. |
| 5,820,592 A | 10/1998 | Hammerslag |
| 5,820,631 A | 10/1998 | Nobles |
| 5,823,955 A | 10/1998 | Kuck et al. |
| 5,823,956 A | 10/1998 | Roth et al. |
| 5,824,065 A | 10/1998 | Gross |
| 5,827,237 A | 10/1998 | Macoviak et al. |
| 5,829,447 A | 11/1998 | Stevens et al. |
| 5,833,671 A | 11/1998 | Macoviak et al. |
| 5,836,955 A | 11/1998 | Buelna et al. |
| 5,840,081 A | 11/1998 | Andersen et al. |
| 5,843,031 A | 12/1998 | Hermann et al. |
| 5,843,178 A | 12/1998 | Vanney et al. |
| 5,849,019 A | 12/1998 | Yoon |
| 5,853,422 A | 12/1998 | Huebsch et al. |
| 5,855,271 A | 1/1999 | Eubanks et al. |
| 5,855,590 A | 1/1999 | Malecki et al. |
| 5,855,601 A | 1/1999 | Bessler et al. |
| 5,855,614 A | 1/1999 | Stevens et al. |
| 5,860,990 A | 1/1999 | Nobles et al. |
| 5,861,003 A | 1/1999 | Latson et al. |
| 5,868,733 A | 2/1999 | Ockuly et al. |
| 5,876,399 A | 3/1999 | Chia et al. |
| 5,879,307 A | 3/1999 | Chio et al. |
| 5,885,258 A | 3/1999 | Sachdeva et al. |
| 5,885,271 A | 3/1999 | Hamilton et al. |
| 5,891,160 A | 4/1999 | Williamson, IV et al. |
| 5,916,147 A | 6/1999 | Boury |
| 5,928,224 A | 7/1999 | Laufer |
| 5,944,733 A | 8/1999 | Engelson |
| 5,947,363 A | 9/1999 | Bolduc et al. |
| 5,954,732 A | 9/1999 | Hart et al. |
| 5,957,949 A | 9/1999 | Leonhard et al. |
| 5,972,020 A | 10/1999 | Carpentier et al. |
| 5,972,030 A | 10/1999 | Garrison et al. |
| 5,976,159 A | 11/1999 | Bolduc et al. |
| 5,980,455 A | 11/1999 | Daniel et al. |
| 5,989,284 A | 11/1999 | Laufer |
| 6,007,552 A | 12/1999 | Fogarty et al. |
| 6,015,417 A | 1/2000 | Reynolds, Jr. |
| 6,017,358 A | 1/2000 | Yoon et al. |
| 6,019,722 A | 2/2000 | Spence et al. |
| 6,022,360 A | 2/2000 | Reimels et al. |
| 6,033,378 A | 3/2000 | Lundquist et al. |
| 6,036,699 A | 3/2000 | Andreas et al. |
| 6,048,351 A | 4/2000 | Gordon et al. |
| 6,056,769 A | 5/2000 | Epstein et al. |
| 6,059,757 A | 5/2000 | Macoviak et al. |
| 6,060,628 A | 5/2000 | Aoyama et al. |
| 6,060,629 A | 5/2000 | Pham et al. |
| 6,063,106 A | 5/2000 | Gibson |
| 6,066,146 A | 5/2000 | Carroll et al. |
| 6,068,628 A | 5/2000 | Fanton et al. |
| 6,068,629 A | 5/2000 | Haissaguerre et al. |
| 6,077,214 A | 6/2000 | Mortier et al. |
| 6,079,414 A | 6/2000 | Roth |
| 6,086,600 A | 7/2000 | Kortenbach |
| 6,088,889 A | 7/2000 | Luther et al. |
| 6,099,505 A | 8/2000 | Ryan et al. |
| 6,099,553 A | 8/2000 | Hart et al. |
| 6,110,145 A | 8/2000 | Macoviak |
| 6,117,144 A | 9/2000 | Nobles et al. |
| 6,117,159 A | 9/2000 | Huebsch et al. |
| 6,120,496 A | 9/2000 | Whayne et al. |
| 6,123,699 A | 9/2000 | Webster, Jr. |
| 6,126,658 A | 10/2000 | Baker |
| 6,132,447 A | 10/2000 | Dorsey |
| 6,136,010 A | 10/2000 | Modesitt et al. |
| 6,143,024 A | 11/2000 | Campbell et al. |
| 6,149,658 A | 11/2000 | Gardiner et al. |
| 6,156,055 A | 12/2000 | Ravenscroft |
| 6,159,240 A | 12/2000 | Sparer et al. |
| 6,162,233 A | 12/2000 | Williamson, IV et al. |
| 6,165,164 A | 12/2000 | Hill et al. |
| 6,165,183 A | 12/2000 | Kuehn et al. |
| 6,165,204 A | 12/2000 | Levinson et al. |
| 6,168,614 B1 | 1/2001 | Andersen et al. |
| 6,171,320 B1 | 1/2001 | Monassevitch |
| 6,182,664 B1 | 2/2001 | Cosgrove |
| 6,187,003 B1 | 2/2001 | Buysse et al. |
| 6,190,408 B1 | 2/2001 | Melvin |
| 6,193,734 B1 | 2/2001 | Bolduc et al. |
| 6,200,315 B1 | 3/2001 | Gaiser et al. |
| 6,203,531 B1 | 3/2001 | Ockuly et al. |
| 6,203,553 B1 | 3/2001 | Robertson et al. |
| 6,206,893 B1 | 3/2001 | Klein et al. |
| 6,206,907 B1 | 3/2001 | Marino et al. |
| 6,210,419 B1 | 4/2001 | Mayenberger et al. |
| 6,210,432 B1 | 4/2001 | Solem et al. |
| 6,217,528 B1 | 4/2001 | Koblish et al. |

(56) References Cited

U.S. PATENT DOCUMENTS

| | | |
|---|---|---|
| 6,245,079 B1 | 6/2001 | Nobles et al. |
| 6,267,746 B1 | 7/2001 | Bumbalough |
| 6,267,781 B1 | 7/2001 | Tu |
| 6,269,819 B1 | 8/2001 | Oz et al. |
| 6,277,555 B1 | 8/2001 | Duran et al. |
| 6,283,127 B1 | 9/2001 | Sterman et al. |
| 6,283,962 B1 | 9/2001 | Tu et al. |
| 6,290,674 B1 | 9/2001 | Roue et al. |
| 6,299,637 B1 | 10/2001 | Shaolian et al. |
| 6,306,133 B1 | 10/2001 | Tu et al. |
| 6,312,447 B1 | 11/2001 | Grimes |
| 6,319,250 B1 | 11/2001 | Falwell et al. |
| 6,322,559 B1 | 11/2001 | Daulton et al. |
| 6,332,880 B1 | 12/2001 | Yang et al. |
| 6,332,893 B1 | 12/2001 | Mortier et al. |
| 6,346,074 B1 | 2/2002 | Roth |
| 6,352,708 B1 | 3/2002 | Duran et al. |
| 6,355,030 B1 | 3/2002 | Aldrich et al. |
| 6,358,277 B1 | 3/2002 | Duran |
| 6,368,326 B1 | 4/2002 | Dakin et al. |
| 6,387,104 B1 | 5/2002 | Pugsley, Jr. et al. |
| 6,402,780 B2 | 6/2002 | Williamson et al. |
| 6,402,781 B1 | 6/2002 | Langberg et al. |
| 6,406,420 B1 | 6/2002 | McCarthy et al. |
| 6,419,669 B1 | 7/2002 | Frazier et al. |
| 6,419,696 B1 | 7/2002 | Ortiz et al. |
| 6,461,366 B1 | 10/2002 | Seguin |
| 6,464,707 B1 | 10/2002 | Bjerken |
| 6,482,224 B1 | 11/2002 | Michler et al. |
| 6,485,489 B2 | 11/2002 | Teirstein et al. |
| 6,508,828 B1 | 1/2003 | Akerfeldt et al. |
| 6,533,796 B1 | 3/2003 | Sauer et al. |
| 6,537,314 B2 | 3/2003 | Langberg et al. |
| 6,540,755 B2 | 4/2003 | Ockuly et al. |
| 6,544,215 B1 | 4/2003 | Bencini et al. |
| 6,551,303 B1 | 4/2003 | Van Tassel et al. |
| 6,551,331 B2 | 4/2003 | Nobles et al. |
| 6,562,037 B2 | 5/2003 | Paton et al. |
| 6,562,052 B2 | 5/2003 | Nobles et al. |
| 6,575,971 B2 | 6/2003 | Hauck et al. |
| 6,585,761 B2 | 7/2003 | Taheri |
| 6,599,311 B1 | 7/2003 | Biggs et al. |
| 6,616,684 B1 | 9/2003 | Vidlund et al. |
| 6,619,291 B2 | 9/2003 | Hlavka et al. |
| 6,626,899 B2 | 9/2003 | Houser et al. |
| 6,626,930 B1 | 9/2003 | Allen et al. |
| 6,629,534 B1 | 10/2003 | St. Goar et al. |
| 6,641,592 B1 | 11/2003 | Sauer et al. |
| 6,656,221 B2 | 12/2003 | Taylor et al. |
| 6,669,687 B1 | 12/2003 | Saadat |
| 6,685,648 B2 | 2/2004 | Flaherty et al. |
| 6,689,164 B1 | 2/2004 | Seguin |
| 6,695,866 B1 | 2/2004 | Kuehn et al. |
| 6,701,929 B2 | 3/2004 | Hussein |
| 6,702,825 B2 | 3/2004 | Frazier et al. |
| 6,702,826 B2 | 3/2004 | Liddicoat et al. |
| 6,709,382 B1 | 3/2004 | Horner |
| 6,709,456 B2 | 3/2004 | Langberg et al. |
| 6,718,985 B2 | 4/2004 | Hlavka et al. |
| 6,719,767 B1 | 4/2004 | Kimblad |
| 6,723,038 B1 | 4/2004 | Schroeder et al. |
| 6,726,716 B2 | 4/2004 | Marquez |
| 6,740,107 B2 | 5/2004 | Loeb et al. |
| 6,746,471 B2 | 6/2004 | Mortier et al. |
| 6,752,813 B2 | 6/2004 | Goldfarb et al. |
| 6,755,777 B2 | 6/2004 | Schweich et al. |
| 6,764,510 B2 | 7/2004 | Vidlund et al. |
| 6,767,349 B2 | 7/2004 | Ouchi |
| 6,770,083 B2 | 8/2004 | Seguin |
| 6,797,001 B2 | 9/2004 | Mathis et al. |
| 6,797,002 B2 | 9/2004 | Spence et al. |
| 6,837,867 B2 | 1/2005 | Kortelling |
| 6,855,137 B2 | 2/2005 | Bon |
| 6,860,179 B2 | 3/2005 | Hopper et al. |
| 6,875,224 B2 | 4/2005 | Grimes |
| 6,908,481 B2 | 6/2005 | Cribier |
| 6,926,715 B1 | 8/2005 | Hauck et al. |
| 6,926,730 B1 | 8/2005 | Nguyen et al. |
| 6,945,978 B1 | 9/2005 | Hyde |
| 6,949,122 B2 | 9/2005 | Adams et al. |
| 6,966,914 B2 | 11/2005 | Abe |
| 6,986,775 B2 | 1/2006 | Morales et al. |
| 7,004,970 B2 | 2/2006 | Cauthen, III et al. |
| 7,011,669 B2 | 3/2006 | Kimblad |
| 7,048,754 B2 | 5/2006 | Martin et al. |
| 7,101,395 B2 | 9/2006 | Tremulis et al. |
| 7,112,207 B2 | 9/2006 | Allen et al. |
| 7,226,467 B2 | 6/2007 | Lucatero et al. |
| 7,288,097 B2 | 10/2007 | Seguin |
| 7,381,210 B2 | 6/2008 | Zarbatany et al. |
| 7,464,712 B2 | 12/2008 | Oz et al. |
| 7,497,822 B1 | 3/2009 | Kugler et al. |
| 7,513,908 B2 | 4/2009 | Lattouf |
| 7,533,790 B1 | 5/2009 | Knodel et al. |
| 7,563,267 B2 | 7/2009 | Goldfarb et al. |
| 7,563,273 B2 | 7/2009 | Goldfarb et al. |
| 7,569,062 B1 | 8/2009 | Kuehn et al. |
| 7,604,646 B2 | 10/2009 | Goldfarb et al. |
| 7,608,091 B2 | 10/2009 | Goldfarb et al. |
| 7,635,329 B2 | 12/2009 | Goldfarb et al. |
| 7,651,502 B2 | 1/2010 | Jackson |
| 7,655,015 B2 | 2/2010 | Goldfarb et al. |
| 7,655,040 B2 | 2/2010 | Douk et al. |
| 7,666,204 B2 | 2/2010 | Thornton et al. |
| 7,704,269 B2 | 4/2010 | St. Goar et al. |
| 7,798,953 B1 | 9/2010 | Wilk |
| 7,811,296 B2 | 10/2010 | Goldfarb et al. |
| 7,914,544 B2 | 3/2011 | Nguyen et al. |
| 7,972,323 B1 | 7/2011 | Bencini et al. |
| 7,972,330 B2 | 7/2011 | Alejandro et al. |
| 8,029,565 B2 | 10/2011 | Lattouf |
| 8,052,592 B2 | 11/2011 | Goldfarb et al. |
| 8,062,313 B2 | 11/2011 | Kimblad |
| 8,118,822 B2 | 2/2012 | Schaller et al. |
| 8,216,256 B2 | 7/2012 | Raschdorf, Jr. et al. |
| 8,348,963 B2 | 1/2013 | Wilson et al. |
| 8,940,001 B2 | 1/2015 | Catanese, III et al. |
| 9,572,666 B2 | 2/2017 | Basude et al. |
| 2001/0004715 A1 | 6/2001 | Duran et al. |
| 2001/0005787 A1 | 6/2001 | Oz et al. |
| 2001/0010005 A1 | 7/2001 | Kammerer et al. |
| 2001/0018611 A1 | 8/2001 | Solem et al. |
| 2001/0022872 A1 | 9/2001 | Marui |
| 2001/0037084 A1 | 11/2001 | Nardeo |
| 2001/0039411 A1 | 11/2001 | Johansson et al. |
| 2001/0044568 A1 | 11/2001 | Langberg et al. |
| 2002/0013571 A1 | 1/2002 | Goldfarb et al. |
| 2002/0022848 A1 | 2/2002 | Garrison et al. |
| 2002/0026233 A1 | 2/2002 | Shaknovich |
| 2002/0035361 A1 | 3/2002 | Houser et al. |
| 2002/0035381 A1 | 3/2002 | Bardy et al. |
| 2002/0042651 A1 | 4/2002 | Liddicoat et al. |
| 2002/0055767 A1 | 5/2002 | Forde et al. |
| 2002/0055774 A1 | 5/2002 | Liddicoat |
| 2002/0055775 A1 | 5/2002 | Carpentier et al. |
| 2002/0058910 A1 | 5/2002 | Hermann et al. |
| 2002/0058995 A1 | 5/2002 | Stevens |
| 2002/0077687 A1 | 6/2002 | Ahn |
| 2002/0082621 A1 | 6/2002 | Schurr et al. |
| 2002/0087148 A1 | 7/2002 | Brock et al. |
| 2002/0087169 A1 | 7/2002 | Brock et al. |
| 2002/0087173 A1 | 7/2002 | Alferness et al. |
| 2002/0103532 A1 | 8/2002 | Langberg et al. |
| 2002/0107534 A1 | 8/2002 | Schaefer et al. |
| 2002/0133178 A1 | 9/2002 | Muramatsu et al. |
| 2002/0147456 A1 | 10/2002 | Diduch et al. |
| 2002/0156526 A1 | 10/2002 | Hlavka et al. |
| 2002/0158528 A1 | 10/2002 | Tsuzaki et al. |
| 2002/0161378 A1 | 10/2002 | Downing |
| 2002/0169360 A1 | 11/2002 | Taylor et al. |
| 2002/0183766 A1 | 12/2002 | Seguin |
| 2002/0183787 A1 | 12/2002 | Wahr et al. |
| 2002/0183835 A1 | 12/2002 | Taylor et al. |
| 2003/0005797 A1 | 1/2003 | Hopper et al. |

(56) References Cited

U.S. PATENT DOCUMENTS

| | | |
|---|---|---|
| 2003/0018358 A1 | 1/2003 | Saadat |
| 2003/0045778 A1 | 3/2003 | Ohline et al. |
| 2003/0050693 A1 | 3/2003 | Quijano et al. |
| 2003/0069570 A1 | 4/2003 | Witzel et al. |
| 2003/0069593 A1 | 4/2003 | Tremulis et al. |
| 2003/0069636 A1 | 4/2003 | Solem et al. |
| 2003/0074012 A1 | 4/2003 | Nguyen et al. |
| 2003/0078654 A1 | 4/2003 | Taylor et al. |
| 2003/0083742 A1 | 5/2003 | Spence et al. |
| 2003/0105519 A1 | 6/2003 | Fasol et al. |
| 2003/0105520 A1 | 6/2003 | Alferness et al. |
| 2003/0120340 A1 | 6/2003 | Lisk et al. |
| 2003/0120341 A1 | 6/2003 | Shennib et al. |
| 2003/0130669 A1 | 7/2003 | Damarati |
| 2003/0130694 A1* | 7/2003 | Bojarski .............. A61F 2/0805 606/228 |
| 2003/0130730 A1 | 7/2003 | Cohn et al. |
| 2003/0144697 A1 | 7/2003 | Mathis et al. |
| 2003/0167071 A1 | 9/2003 | Martin et al. |
| 2003/0171776 A1 | 9/2003 | Adams et al. |
| 2003/0187467 A1 | 10/2003 | Schreck |
| 2003/0195562 A1 | 10/2003 | Collier et al. |
| 2003/0208231 A1 | 11/2003 | Williamson, IV et al. |
| 2003/0225423 A1 | 12/2003 | Huitema |
| 2003/0229395 A1 | 12/2003 | Cox |
| 2003/0233038 A1 | 12/2003 | Hassett |
| 2004/0002719 A1 | 1/2004 | Oz et al. |
| 2004/0003819 A1 | 1/2004 | St. Goar et al. |
| 2004/0019377 A1 | 1/2004 | Taylor et al. |
| 2004/0019378 A1 | 1/2004 | Hlavka et al. |
| 2004/0024414 A1 | 2/2004 | Downing |
| 2004/0030382 A1 | 2/2004 | St. Goar et al. |
| 2004/0034365 A1 | 2/2004 | Lentz et al. |
| 2004/0039442 A1 | 2/2004 | St. Goar et al. |
| 2004/0039443 A1 | 2/2004 | Solem et al. |
| 2004/0044350 A1 | 3/2004 | Martin et al. |
| 2004/0044365 A1 | 3/2004 | Bachman |
| 2004/0049207 A1 | 3/2004 | Goldfarb et al. |
| 2004/0049211 A1 | 3/2004 | Tremulis et al. |
| 2004/0073302 A1 | 4/2004 | Rourke et al. |
| 2004/0078053 A1 | 4/2004 | Berg et al. |
| 2004/0087975 A1 | 5/2004 | Lucatero et al. |
| 2004/0088047 A1 | 5/2004 | Spence et al. |
| 2004/0092962 A1 | 5/2004 | Thornton et al. |
| 2004/0093023 A1 | 5/2004 | Allen et al. |
| 2004/0097878 A1 | 5/2004 | Anderson et al. |
| 2004/0097979 A1 | 5/2004 | Svanidze et al. |
| 2004/0106989 A1 | 6/2004 | Wilson et al. |
| 2004/0111099 A1 | 6/2004 | Nguyen et al. |
| 2004/0122448 A1 | 6/2004 | Levine |
| 2004/0127981 A1 | 7/2004 | Randert et al. |
| 2004/0127982 A1 | 7/2004 | Machold et al. |
| 2004/0127983 A1 | 7/2004 | Mortier et al. |
| 2004/0133062 A1 | 7/2004 | Pai et al. |
| 2004/0133063 A1 | 7/2004 | McCarthy et al. |
| 2004/0133082 A1 | 7/2004 | Abraham-Fuchs et al. |
| 2004/0133192 A1 | 7/2004 | Houser et al. |
| 2004/0133220 A1 | 7/2004 | Lashinski et al. |
| 2004/0133240 A1 | 7/2004 | Adams et al. |
| 2004/0133273 A1 | 7/2004 | Cox |
| 2004/0138744 A1 | 7/2004 | Lashinski et al. |
| 2004/0138745 A1 | 7/2004 | Macoviak et al. |
| 2004/0148021 A1 | 7/2004 | Cartledge et al. |
| 2004/0152847 A1 | 8/2004 | Emri et al. |
| 2004/0152947 A1 | 8/2004 | Schroeder et al. |
| 2004/0153144 A1 | 8/2004 | Seguin |
| 2004/0158123 A1 | 8/2004 | Jayaraman |
| 2004/0162610 A1 | 8/2004 | Laiska et al. |
| 2004/0167539 A1 | 8/2004 | Kuehn et al. |
| 2004/0186486 A1 | 9/2004 | Roue et al. |
| 2004/0186566 A1 | 9/2004 | Hindrichs et al. |
| 2004/0193191 A1 | 9/2004 | Starksen et al. |
| 2004/0215339 A1 | 10/2004 | Drasler et al. |
| 2004/0220593 A1 | 11/2004 | Greenhalgh |
| 2004/0220657 A1 | 11/2004 | Nieminen et al. |
| 2004/0225300 A1 | 11/2004 | Goldfarb et al. |
| 2004/0236354 A1 | 11/2004 | Seguin |
| 2004/0243229 A1 | 12/2004 | Vidlund et al. |
| 2004/0249452 A1 | 12/2004 | Adams et al. |
| 2004/0249453 A1 | 12/2004 | Cartledge et al. |
| 2004/0260393 A1 | 12/2004 | Randert et al. |
| 2005/0004583 A1 | 1/2005 | Oz et al. |
| 2005/0004665 A1 | 1/2005 | Aklog |
| 2005/0004668 A1 | 1/2005 | Aklog et al. |
| 2005/0021056 A1 | 1/2005 | St. Goer et al. |
| 2005/0021057 A1 | 1/2005 | St. Goer et al. |
| 2005/0021058 A1 | 1/2005 | Negro |
| 2005/0033446 A1 | 2/2005 | Deem et al. |
| 2005/0038508 A1 | 2/2005 | Gabbay |
| 2005/0049698 A1 | 3/2005 | Bolling et al. |
| 2005/0055089 A1 | 3/2005 | Macoviak et al. |
| 2005/0059351 A1 | 3/2005 | Cauwels et al. |
| 2005/0149014 A1 | 7/2005 | Hauck et al. |
| 2005/0159810 A1 | 7/2005 | Filsoufi |
| 2005/0197694 A1 | 9/2005 | Pai et al. |
| 2005/0197695 A1 | 9/2005 | Stacchino et al. |
| 2005/0216039 A1 | 9/2005 | Lederman |
| 2005/0228422 A1 | 10/2005 | Machold et al. |
| 2005/0228495 A1 | 10/2005 | Macoviak |
| 2005/0251001 A1 | 11/2005 | Hassett |
| 2005/0267493 A1 | 12/2005 | Schreck et al. |
| 2005/0273160 A1 | 12/2005 | Lashinski et al. |
| 2005/0287493 A1 | 12/2005 | Novak et al. |
| 2006/0004247 A1 | 1/2006 | Kute et al. |
| 2006/0015003 A1 | 1/2006 | Moaddes et al. |
| 2006/0020275 A1 | 1/2006 | Goldfarb et al. |
| 2006/0030866 A1 | 2/2006 | Schreck |
| 2006/0030867 A1 | 2/2006 | Zadno |
| 2006/0030885 A1 | 2/2006 | Hyde |
| 2006/0058871 A1 | 3/2006 | Zakay et al. |
| 2006/0064115 A1 | 3/2006 | Allen et al. |
| 2006/0064116 A1 | 3/2006 | Allen et al. |
| 2006/0064118 A1 | 3/2006 | Kimblad |
| 2006/0089671 A1 | 4/2006 | Goldfarb et al. |
| 2006/0089711 A1 | 4/2006 | Dolan |
| 2006/0135993 A1 | 6/2006 | Seguin |
| 2006/0184203 A1 | 8/2006 | Martin et al. |
| 2006/0190036 A1 | 8/2006 | Wendel et al. |
| 2006/0195012 A1 | 8/2006 | Mortier et al. |
| 2006/0229708 A1 | 10/2006 | Powell et al. |
| 2006/0252984 A1 | 11/2006 | Randert et al. |
| 2006/0293701 A1 | 12/2006 | Ainsworth et al. |
| 2007/0038293 A1 | 2/2007 | St. Goar et al. |
| 2007/0100356 A1 | 5/2007 | Lucatero et al. |
| 2007/0118155 A1 | 5/2007 | Goldfarb et al. |
| 2007/0129737 A1 | 6/2007 | Goldfarb et al. |
| 2007/0162125 A1 | 7/2007 | LeBeau et al. |
| 2007/0197858 A1 | 8/2007 | Goldfarb et al. |
| 2007/0198082 A1 | 8/2007 | Kapadia et al. |
| 2007/0213747 A1 | 9/2007 | Monassevitch et al. |
| 2008/0039935 A1 | 2/2008 | Buch et al. |
| 2008/0051703 A1 | 2/2008 | Thornton et al. |
| 2008/0051807 A1 | 2/2008 | St. Goar et al. |
| 2008/0097489 A1 | 4/2008 | Goldfarb et al. |
| 2008/0167714 A1 | 7/2008 | St. Goer et al. |
| 2008/0183194 A1 | 7/2008 | Goldfarb et al. |
| 2009/0156995 A1 | 6/2009 | Martin et al. |
| 2009/0163934 A1 | 6/2009 | Raschdorf et al. |
| 2009/0177266 A1 | 7/2009 | Powell et al. |
| 2009/0182419 A1 | 7/2009 | Bolling |
| 2009/0198322 A1 | 8/2009 | Deem et al. |
| 2009/0270858 A1 | 10/2009 | Hauck et al. |
| 2009/0326567 A1 | 12/2009 | Goldfarb et al. |
| 2010/0016899 A1* | 1/2010 | Gelfand .............. A61B 17/8061 606/280 |
| 2010/0016958 A1 | 1/2010 | St. Goer et al. |
| 2010/0022823 A1 | 1/2010 | Goldfarb et al. |
| 2010/0152753 A1 | 6/2010 | Menn et al. |
| 2010/0324585 A1 | 12/2010 | Miles et al. |
| 2012/0296349 A1 | 11/2012 | Smith et al. |
| 2013/0035759 A1 | 2/2013 | Gross et al. |
| 2013/0066341 A1 | 3/2013 | Ketai et al. |
| 2013/0066342 A1 | 3/2013 | Dell et al. |
| 2013/0073029 A1 | 3/2013 | Shaw |

(56) References Cited

U.S. PATENT DOCUMENTS

| | | |
|---|---|---|
| 2013/0138121 A1 | 5/2013 | Allen et al. |
| 2013/0253642 A1 | 9/2013 | Brecker |
| 2013/0261638 A1 | 10/2013 | Diamant et al. |
| 2014/0066693 A1 | 3/2014 | Goldfarb et al. |
| 2014/0067054 A1 | 3/2014 | Chau et al. |
| 2014/0249553 A1 | 9/2014 | Kimura et al. |
| 2014/0309670 A1 | 10/2014 | Bakos et al. |
| 2015/0005809 A1 | 1/2015 | Ayres et al. |
| 2015/0073473 A1 | 3/2015 | Broom et al. |
| 2015/0223793 A1 | 8/2015 | Goldfarb et al. |
| 2015/0257877 A1 | 9/2015 | Hernandez |
| 2016/0174979 A1 | 6/2016 | Wei |
| 2016/0287387 A1 | 10/2016 | Wei |
| 2017/0020521 A1 | 1/2017 | Krone et al. |
| 2018/0146966 A1 | 5/2018 | Hernandez et al. |
| 2018/0161159 A1 | 6/2018 | Lee et al. |

FOREIGN PATENT DOCUMENTS

| | | |
|---|---|---|
| DE | 3504292 | 7/1986 |
| DE | 3504292 C1 | 7/1986 |
| DE | 19810696 | 5/1999 |
| DE | 19810696 C1 | 5/1999 |
| DE | 101 16 168 A1 | 11/2001 |
| DE | 10116168 | 11/2001 |
| EP | 0 179 562 B1 | 7/1989 |
| EP | 0179562 | 7/1989 |
| EP | 0 558 031 B1 | 2/1993 |
| EP | 0558031 | 2/1993 |
| EP | 0 558 031 A2 | 9/1993 |
| EP | 0 684 012 A2 | 11/1995 |
| EP | 0684012 | 11/1995 |
| EP | 0 727 239 A2 | 8/1996 |
| EP | 0727239 | 8/1996 |
| EP | 0 782 836 A1 | 7/1997 |
| EP | 0782836 | 7/1997 |
| EP | 1 199 037 A2 | 4/2002 |
| EP | 1199037 | 4/2002 |
| EP | 1 230 899 A1 | 8/2002 |
| EP | 1230899 | 8/2002 |
| EP | 1383448 A2 | 1/2004 |
| EP | 1 674 040 A2 | 6/2006 |
| EP | 1674040 | 6/2006 |
| FR | 2 768 324 A1 | 3/1999 |
| FR | 2768324 | 3/1999 |
| FR | 2768324 A1 | 3/1999 |
| GB | 1 598 111 A | 9/1981 |
| GB | 1598111 | 9/1981 |
| GB | 2 151 142 A | 7/1985 |
| GB | 2151142 | 7/1985 |
| JP | 9-192137 A | 7/1997 |
| JP | 09-253030 A | 9/1997 |
| JP | H 09253030 | 9/1997 |
| JP | 11-089937 A | 4/1999 |
| JP | H 11089937 | 4/1999 |
| JP | 2000-283130 A | 10/2000 |
| JP | 2000283130 | 10/2000 |
| JP | 2002-540878 A | 12/2002 |
| JP | 2006-528911 A | 12/2006 |
| JP | 2015502548 | 1/2015 |
| JP | 59-85653 B2 | 9/2016 |
| WO | WO 81/00668 A1 | 3/1981 |
| WO | WO 1981000668 | 3/1981 |
| WO | WO 91/01689 A1 | 2/1991 |
| WO | WO 1991001689 | 2/1991 |
| WO | WO 91/18881 A1 | 12/1991 |
| WO | WO 1991018881 | 12/1991 |
| WO | WO 92/12690 A1 | 8/1992 |
| WO | WO 1992012690 | 8/1992 |
| WO | WO 94/18881 A1 | 9/1994 |
| WO | WO 94/18893 A1 | 9/1994 |
| WO | WO 1994018881 | 9/1994 |
| WO | WO 1994018893 | 9/1994 |
| WO | WO 95/11620 A2 | 5/1995 |
| WO | WO 1995011620 | 5/1995 |
| WO | WO 95/15715 A1 | 6/1995 |
| WO | WO 1995015715 | 6/1995 |
| WO | WO 96/14032 A1 | 5/1996 |
| WO | WO 1996014032 | 5/1996 |
| WO | WO 96/20655 A1 | 7/1996 |
| WO | WO 1996020655 | 7/1996 |
| WO | WO 96/22735 A1 | 8/1996 |
| WO | WO 1996022735 | 8/1996 |
| WO | WO 96/30072 A1 | 10/1996 |
| WO | WO 96/32882 A1 | 10/1996 |
| WO | WO 1996030072 | 10/1996 |
| WO | WO 97/18746 A2 | 5/1997 |
| WO | WO 1997018746 | 5/1997 |
| WO | WO 97/25927 A1 | 7/1997 |
| WO | WO 97/26034 A1 | 7/1997 |
| WO | WO 1997025927 | 7/1997 |
| WO | WO 1997026034 | 7/1997 |
| WO | WO 97/27807 A1 | 8/1997 |
| WO | WO 97/38748 A2 | 10/1997 |
| WO | WO 97/39688 A2 | 10/1997 |
| WO | WO 1997038748 | 10/1997 |
| WO | WO 1997039688 | 10/1997 |
| WO | WO 97/48436 A2 | 12/1997 |
| WO | WO 1997048436 | 12/1997 |
| WO | WO 98/07375 A1 | 2/1998 |
| WO | WO 1998007375 | 2/1998 |
| WO | WO 98/24372 A1 | 6/1998 |
| WO | WO 1998024372 | 6/1998 |
| WO | WO 98/30153 A1 | 7/1998 |
| WO | WO 98/32382 A1 | 7/1998 |
| WO | WO 1998030153 | 7/1998 |
| WO | WO 1998032382 | 7/1998 |
| WO | WO 98/35638 A1 | 8/1998 |
| WO | WO 1998035638 | 8/1998 |
| WO | WO 99/00059 A1 | 1/1999 |
| WO | WO 99/01377 A1 | 1/1999 |
| WO | WO 1999000059 | 1/1999 |
| WO | WO 1999001377 | 1/1999 |
| WO | WO 99/07354 A2 | 2/1999 |
| WO | WO 1999007354 | 2/1999 |
| WO | WO 99/13777 A1 | 3/1999 |
| WO | WO 1999013777 | 3/1999 |
| WO | WO 99/15223 A1 | 4/1999 |
| WO | WO 99/66967 A1 | 12/1999 |
| WO | WO 1999066967 | 12/1999 |
| WO | WO 00/02489 A1 | 1/2000 |
| WO | WO 00/03651 A1 | 1/2000 |
| WO | WO 00/03759 A2 | 1/2000 |
| WO | WO 2000002489 | 1/2000 |
| WO | WO 2000003651 | 1/2000 |
| WO | WO 2000003759 | 1/2000 |
| WO | WO 00/12168 A1 | 3/2000 |
| WO | WO 2000012168 | 3/2000 |
| WO | WO 00/44313 A1 | 8/2000 |
| WO | WO 2000044313 | 8/2000 |
| WO | WO 00/59382 A1 | 10/2000 |
| WO | WO 00/60995 A2 | 10/2000 |
| WO | WO 2000059382 | 10/2000 |
| WO | WO 2000060995 | 10/2000 |
| WO | WO 01/00111 A1 | 1/2001 |
| WO | WO 01/00114 A1 | 1/2001 |
| WO | WO 01/03651 A2 | 1/2001 |
| WO | WO 2001000111 | 1/2001 |
| WO | WO 2001000114 | 1/2001 |
| WO | WO 2001003651 | 1/2001 |
| WO | WO 01/26557 A1 | 4/2001 |
| WO | WO 01/26586 A1 | 4/2001 |
| WO | WO 01/26587 A1 | 4/2001 |
| WO | WO 01/26588 A2 | 4/2001 |
| WO | WO 01/26703 A1 | 4/2001 |
| WO | WO 01/28432 A1 | 4/2001 |
| WO | WO 01/28455 A1 | 4/2001 |
| WO | WO 2001026557 | 4/2001 |
| WO | WO 2001026586 | 4/2001 |
| WO | WO 2001026587 | 4/2001 |
| WO | WO 2001026588 | 4/2001 |
| WO | WO 2001026703 | 4/2001 |
| WO | WO 2001028432 | 4/2001 |
| WO | WO 2001028455 | 4/2001 |

(56) References Cited

FOREIGN PATENT DOCUMENTS

| | | | |
|---|---|---|---|
| WO | WO 01/35832 A2 | 5/2001 | |
| WO | WO 01/47438 A1 | 7/2001 | |
| WO | WO 01/49213 A2 | 7/2001 | |
| WO | WO 01/50985 A1 | 7/2001 | |
| WO | WO 2001047438 | 7/2001 | |
| WO | WO 2001049213 | 7/2001 | |
| WO | WO 2001050985 | 7/2001 | |
| WO | WO 01/54618 A1 | 8/2001 | |
| WO | WO 01/56512 A1 | 8/2001 | |
| WO | WO 2001054618 | 8/2001 | |
| WO | WO 2001056512 | 8/2001 | |
| WO | WO 01/66001 A2 | 9/2001 | |
| WO | WO 01/70320 A1 | 9/2001 | |
| WO | WO 2001066001 | 9/2001 | |
| WO | WO 2001070320 | 9/2001 | |
| WO | WO 01/89440 A2 | 11/2001 | |
| WO | WO 2001089440 | 11/2001 | |
| WO | WO 01/95831 A2 | 12/2001 | |
| WO | WO 01/95832 A2 | 12/2001 | |
| WO | WO 01/97741 A2 | 12/2001 | |
| WO | WO 2001095831 | 12/2001 | |
| WO | WO 2001095832 | 12/2001 | |
| WO | WO 2001097741 | 12/2001 | |
| WO | WO 02/00099 A2 | 1/2002 | |
| WO | WO 02/01999 A2 | 1/2002 | |
| WO | WO 02/03892 A1 | 1/2002 | |
| WO | WO 2002000099 | 1/2002 | |
| WO | WO 2002001999 | 1/2002 | |
| WO | WO 2002003892 | 1/2002 | |
| WO | WO 02/34167 A2 | 5/2002 | |
| WO | WO 2002034167 | 5/2002 | |
| WO | WO 02/060352 A1 | 8/2002 | |
| WO | WO 02/062263 A2 | 8/2002 | |
| WO | WO 02/062270 A1 | 8/2002 | |
| WO | WO 02/062408 A2 | 8/2002 | |
| WO | WO 2002060352 | 8/2002 | |
| WO | WO 2002062263 | 8/2002 | |
| WO | WO 2002062270 | 8/2002 | |
| WO | WO 2002062408 | 8/2002 | |
| WO | WO 03/001893 A2 | 1/2003 | |
| WO | WO 03/003930 A1 | 1/2003 | |
| WO | WO 2003001893 | 1/2003 | |
| WO | WO 2003003930 | 1/2003 | |
| WO | WO 03/020179 A1 | 3/2003 | |
| WO | WO 2003020179 | 3/2003 | |
| WO | WO 03/028558 A2 | 4/2003 | |
| WO | WO 2003028558 | 4/2003 | |
| WO | WO 03/037171 A2 | 5/2003 | |
| WO | WO 2003037171 | 5/2003 | |
| WO | WO 03/047467 A1 | 6/2003 | |
| WO | WO 03/049619 A2 | 6/2003 | |
| WO | WO 2003047467 | 6/2003 | |
| WO | WO 2003049619 | 6/2003 | |
| WO | WO 03/073910 A2 | 9/2003 | |
| WO | WO 03/073913 A2 | 9/2003 | |
| WO | WO 2003073910 | 9/2003 | |
| WO | WO 2003073913 | 9/2003 | |
| WO | WO 03/082129 A2 | 10/2003 | |
| WO | WO 2003082129 | 10/2003 | |
| WO | WO 03/105667 A2 | 12/2003 | |
| WO | WO 2003105667 | 12/2003 | |
| WO | WO 2004/004607 A1 | 1/2004 | |
| WO | WO 2004004607 | 1/2004 | |
| WO | WO 2004/012583 A2 | 2/2004 | |
| WO | WO 2004/012789 A2 | 2/2004 | |
| WO | WO 2004/014282 A2 | 2/2004 | |
| WO | WO 2004012583 | 2/2004 | |
| WO | WO 2004012789 | 2/2004 | |
| WO | WO 2004014282 | 2/2004 | |
| WO | WO 2004/019811 A2 | 3/2004 | |
| WO | WO 2004019811 | 3/2004 | |
| WO | WO 2004/030570 A2 | 4/2004 | |
| WO | WO 2004030570 | 4/2004 | |
| WO | WO 2004/037317 A2 | 5/2004 | |
| WO | WO 2004037317 | 5/2004 | |
| WO | WO 2004/045370 A2 | 6/2004 | |
| WO | WO 2004/045378 A2 | 6/2004 | |
| WO | WO 2004/045463 A2 | 6/2004 | |
| WO | WO 2004/047679 A1 | 6/2004 | |
| WO | WO 2004045370 | 6/2004 | |
| WO | WO 2004045378 | 6/2004 | |
| WO | WO 2004045463 | 6/2004 | |
| WO | WO 2004047679 | 6/2004 | |
| WO | WO 2004/062725 A1 | 7/2004 | |
| WO | WO 2004062725 | 7/2004 | |
| WO | WO 2004/082523 A2 | 9/2004 | |
| WO | WO 2004/082538 A2 | 9/2004 | |
| WO | WO 2004082523 | 9/2004 | |
| WO | WO 2004082538 | 9/2004 | |
| WO | WO 2004/093730 A2 | 11/2004 | |
| WO | WO 2004093730 | 11/2004 | |
| WO | WO 04/103162 A2 | 12/2004 | |
| WO | WO 2004/103162 A2 | 12/2004 | |
| WO | WO 2004/112585 A2 | 12/2004 | |
| WO | WO 2004/112651 A2 | 12/2004 | |
| WO | WO 2004103162 | 12/2004 | |
| WO | WO 2004112585 | 12/2004 | |
| WO | WO 2004112651 | 12/2004 | |
| WO | WO 2005/002424 A2 | 1/2005 | |
| WO | WO 2005002424 | 1/2005 | |
| WO | WO 2005/018507 A2 | 3/2005 | |
| WO | WO 2005/027797 A1 | 3/2005 | |
| WO | WO 2005018507 | 3/2005 | |
| WO | WO 2005027797 | 3/2005 | |
| WO | WO 2005/032421 A2 | 4/2005 | |
| WO | WO 2005032421 | 4/2005 | |
| WO | WO 2005/062931 A2 | 7/2005 | |
| WO | WO 2005062931 | 7/2005 | |
| WO | WO 2005/112792 A2 | 12/2005 | |
| WO | WO 2005112792 | 12/2005 | |
| WO | WO 2006037073 | 4/2006 | |
| WO | WO 2006/105008 A1 | 10/2006 | |
| WO | WO 2006/105009 A1 | 10/2006 | |
| WO | WO 2006105008 | 10/2006 | |
| WO | WO 2006105009 | 10/2006 | |
| WO | WO 2006/115875 A2 | 11/2006 | |
| WO | WO 2006/115876 A2 | 11/2006 | |
| WO | WO 2006115875 | 11/2006 | |
| WO | WO 2006115876 | 11/2006 | |
| WO | WO 2007009099 | 1/2007 | |
| WO | WO 2007038608 | 4/2007 | |
| WO | WO 2008/140439 A1 | 11/2008 | |
| WO | WO 2010/128502 A1 | 11/2010 | |
| WO | WO 2011034973 | 3/2011 | |
| WO | WO 2011/066533 A1 | 6/2011 | |
| WO | WO 2014138482 | 9/2014 | |
| WO | WO 2016161135 | 10/2016 | |
| WO | WO 2017015288 | 1/2017 | |
| WO | WO 2018102310 | 6/2018 | |
| WO | WO 2018106482 | 6/2018 | |

OTHER PUBLICATIONS

Cribier et al., "Percutaneous Mechanical Mitral Commissurotomy With a Newly Designed Metallic Valvulotome: Immediate Results of the Initial Experience in 153 Patients," Circulation 99:793-799 (1999).

Dias de Azeredo Bastos et al., "Percutaneous Mechanical Mitral Commissurotomy Performed With a Cribier's Metallic Valvulotome. Initial Results," Arq Bras Cardiol, 77:126-131 (2001).

Freeny et al., "Subselective Diagnostic and Interventional Arteriography Using a Simple Coaxial Catheter System," Cardiovasc. Intervent. Radiol. 7:209-213 (1984).

Ing et al., "The Snare-Assisted Technique for Transcatheter Coil Occlusion of Moderate to Large Patent Ductus Arteriosus: Immediate and Intermediate Results," J. Am. Col. Cardiol. 33(6):1710-1718 (1999).

Rahhal, "Tiny device to 'zip up' leaky hearts invented by Dr Oz 20 years ago could save millions, study finds," Daily Mail (Sep. 26, 2018).

U.S. Appl. No. 60/316,892 to Tremulis et al., filed Aug. 31, 2001.

(56) References Cited

OTHER PUBLICATIONS

Waller et al., "Anatomic Basis for and Morphologic Results from Catheter Balloon Valvuloplasty of Stenotic Mitral Valves," Clin. Cardiol. 13:655-661 (1990).
Abe et al, De Vega's Annuloplasty for Acquired Tricuspid Disease: Early and Late Results in 110 Patients, Ann. Thorac. Surg., Jan. 1989, pp. 670-676, vol. 48.
Agricola et al., "Mitral Valve Reserve in Double Orifice Technique: an Exercise Echocardiographic Study," Journal of Heart Valve Disease, 11(5):637-643 (2002).
Alfieri et al., "An Effective Technique to Correct Anterior Mitral Leaflet Prolapse," J. Card Surg., 14:468-470 (1999).
Alfieri et al., "Novel Suture Device for Beating Heart Mitral Leaflet Approximation," Annals of Thoracic Surgery, 74:1488-1493 (2002).
Alfieri et al., "The double orifice technique in mitral valve repair: a simple solution for complex problems," Journal of Thoracic and Cardiovascular Surgery, 122:674-681 (2001).
Alfieri et al., "The edge to edge technique," The European Association for Cardio-Thoracic Surgery 14th Annual Meeting, Oct. 7-11, 2000, Book of Proceedings.
Alfieri, "The Edge-to-Edge Repair of the Mitral Valve," [Abstract] 6th Annual New Era Cardiac Care: Innovation & Technology, Heart Surgery Forum, (Jan. 2003) pp. 103.
Ali Khan et al, Blade Atrial Septostomy: Experience with the First 50 Procedures, Cathet. Cardiovasc. Diagn., Aug. 1991, pp. 257-262, vol. 23.
Alvarez et al, Repairing the Degenerative Mitral Valve: Ten to Fifteen-year Follow-up, J. Thorac. Cardiovasc. Surg., Aug. 1996, pp. 238-247, vol. 112.
Arisi et al., "Mitral Valve Repair with Alfieri Technique in Mitral Regurgitation of Diverse Etiology: Early Echocardiographic Results," Circulation Supplement II, 104(17):3240 (2001).
Bach et al, Early Improvement in Congestive Heart Failure After Correction of Secondary Mitral Regurgitation in End-stage Cardiomyopathy, Am. Heart J., Jun. 1995, pp. 1165-1170, vol. 129.
Bach et al, Improvement Following Correction of Secondary Mitral Regurgitation in End-stage Cardiomyopathy With Mitral Annuloplasty, Am. J. Cardiol., Oct. 15, 1996, pp. 966-969, vol. 78.
Bailey, "Mitral Regurgitation" in Surgery of the Heart, Chapter 20, pp. 686-737 (1955).
Bernal et al., "The Valve Racket: a new and different concept of atrioventricular valve repair," Eur. J. Cardio-thoracic Surgery 29:1026-1029 (2006).
Bhudia et al., "Edge-to-Edge (Alfieri) Mitral Repair: Results in Diverse Clinical Settings," Ann Thorac Surg, 77:1598-1606 (2004).
Bhudia, #58 Edge-to-edge mitral repair: a versatile mitral repair technique, 2003 STS Presentation, [Abstract Only], 2004.
Bolling et al, Surgery for Acquired Heart Disease: Early Outcome of Mitral Valve Reconstruction in Patients with End-stage Cardiomyopathy, J. Thor. And Cariovasc. Surg., Apr. 1995, pp. 676-683, vol. 109.
Borghetti et al., "Preliminary observations on haemodynamics during physiological stress conditions following 'double-orifice' mitral valve repair," European Journal of Cardio-thoracic Surgery, 20:262-269 (2001).
Castedo, "Edge-to-Edge Tricuspid Repair for Redeveloped Valve Incompetence after DeVega's Annuloplasty," Ann Thora Surg., 75:605-606 (2003).
Chinese Office Action issued in Chinese Application No. 200980158707.2 dated Sep. 9, 2013.
Communication dated Apr. 16, 2018 from the European Patent Office in counterpart European application No. 04752603.3.
Communication dated Apr. 28, 2017 issued by the European Patent Office in counterpart application No. 16196023.2.
Communication dated Jan. 26, 2017, from the European Patent Office in counterpart European application No. 16196023.2.
Communication dated May 8, 2017, from the European Patent Office in counterpart European Application No. 04752714.8.
Dec et al, Idiopathic Dilated Cardiomyopathy, N. Engl. J. Med., Dec. 8, 1994, pp. 1564-1575, vol. 331.
Dottori et al., "Echocardiographic imaging of the Alfieri type mitral valve repair," Ital. Heart J., 2(4):319-320 (2001).
Downing et al., "Beating heart mitral valve surgery: Preliminary model and methodology," Journal of Thoracic and Cardiovascular Surgery, 123(6):1141-1146 (2002).
Extended European Search Report, dated Oct. 17, 2014, issued in European Patent Application No. 06751584.1.
Falk et al., "Computer-Enhanced Mitral Valve Surgery: Toward a Total Endoscopic Procedure," Seminars in Thoracic and Cardiovascular Surgery, 11(3):244-249 (1999).
Filsoufi et al., "Restoring Optimal Surface of Coaptation With a Mini Leaflet Prosthesis: A New Surgical Concept for the Correction of Mitral Valve Prolapse," Intl. Soc. for Minimally Invasive Cardiothoracic Surgery 1(4):186-87 (2006).
Frazier et al., #62 Early Clinical Experience with an Implantable, Intracardiac Circulatory Support Device: Operative Considerations and Physiologic Implications, 2003 STS Presentation, 1 page total. [Abstract Only].
Fucci et al, Improved Results with Mitral Valve Repair Using New Surgical Techniques, Eur. J. Cardiothorac. Surg., Nov. 1995, pp. 621-627, vol. 9.
Fundaro et al., "Chordal Plication and Free Edge Remodeling for Mitral Anterior Leaflet Prolapse Repair: 8-Year Follow-up," Annals of Thoracic Surgery, 72:1515-1519 (2001).
Garcia-Rinaldi et al., "Left Ventricular Volume Reduction and Reconstruction is Ischemic Cardiomyopathy," Journal of Cardiac Surgery, 14:199-210 (1999).
Gateliene, "Early and postoperative results results of metal and tricuspid valve insufficiency surgical treatment using edge-to-edge central coaptation procedure," (Oct. 2002) 38 (Suppl 2):172-175.
Gatti et al., "The edge to edge technique as a trick to rescue an imperfect mitral valve repair," Eur. J. Cardiothorac Surg, 22:817-820 (2002).
Gillinov et al., "Is Minimally Invasive Heart Valve Surgery a Paradigm for the Future?" Current Cardiology Reports, 1:318-322 (1999).
Gundry, "Facile mitral valve repair utilizing leaflet edge approximation: midterm results of the Alfieri figure of eight repair," Presented at the Meeting of the Western Thoracic Surgical Association, (1999).
Gupta et al., #61 Influence of Older Donor Grafts on Heart Transplant Survival: Lack of Recipient Effects, 2003 STS Presentation, [Abstract Only].
Ikeda et al., "Batista's Operation with Coronary Artery Bypass Grafting and Mitral Valve Plasty for Ischemic Dilated Cardiomyopathy," The Japanese Journal of Thoracic and Cardiovascular Surgery, 48:746-749 (2000).
International Search Report and Written Opinion of PCT Application No. PCT/US2009/068023, dated Mar. 2, 2010, 10 pages total.
Izzat et al., "Early Experience with Partial Left Ventriculectomy in the Asia-Pacific Region," Annals of Thoracic Surgery, 67:1703-1707 (1999).
Kallner et al., "Transaortic Approach for the Alfieri Stitch," Ann Thorac Surg, 71:378-380 (2001).
Kameda et al, Annuloplasty for Severe Mitral Regurgitation Due to Dilated Cardiomyopathy, Ann. Thorac. Surg., 1996, pp. 1829-1832, vol. 61.
Kavarana et al., "Transaortic Repair of Mitral Regurgitation," The Heart Surgery Forum, #2000-2389, 3(1):24-28 (2000).
Kaza et al., "Ventricular Reconstruction Results in Improved Left Ventricular Function and Amelioration of Mitral Insufficiency," Annals of Surgery, 235(6):828-832 (2002).
Kherani et al., "The Edge-To-Edge Mitral Valve Repair: The Columbia Presbyterian Experience," Ann. Thorac. Surg., 78:73-76 (2004).
Konertz et al., "Results After Partial Left Ventriculectomy in a European Heart Failure Population," Journal of Cardiac Surgery, 14:129-135 (1999).
Kron et al., "Surgical Relocation of the Posterior Papillary Muscle in Chronic Ischemic Mitral Regurgitation," Annals. Of Thoracic Surgery, 74:600-601 (2002).
Kruger et al., "P73—Edge to Edge Technique in Complex Mitral Valve Repair," Thorac Cardiovasc Surg., 48(Suppl. 1):106 (2000).

(56) References Cited

OTHER PUBLICATIONS

Langer et al., "Posterier mitral leaflet extensions: An adjunctive repair option for ischemic mitral regurgitation?" J Thorac Cardiovasc Surg, 131:868-877 (2006)
Lorusso et al., "'Double-Orifice' Technique to Repair Extensive Mitral Valve Excision Following Acute Endocarditis," J. Card Surg, 13:24-26 (1998).
Lorusso et al., "The double-orifice technique for mitral valve reconstruction: predictors of postoperative outcome," Eur J. Cardiothorac Surg, 20:583-589 (2001).
Maisano et al., "The double orifice repair for Barlow Disease: a simple solution for a complex repair," Supplement I Circulation, (Nov. 1999); 100(18):1-94.
Maisano et al., "The double orifice technique as a standardized approach to treat mitral regurgitation due to severe myxomatous disease: surgical technique," European Journal of Cardio-thoracic Surgery, 17:201-205 (2000).
Maisano et al, The Edge-to-edge Technique: A Simplified Method to Correct Mitral Insufficiency, Eur. J. Cardiothorac. Surg., Jan. 14, 1998, pp. 240-246, vol. 13.
Maisano et al., "The hemodynamic effects of double-orifice valve repair for mitral regurgitation: a 3D computational model," European Journal of Cardio-thoracic Surgery, 15:419-425 (1999).
Maisano et al., "Valve repair for traumatic tricuspid regurgitation," Eur. J. Cardio-thorac Surg, 10:867-873 (1996).
Mantovani et al., "Edge-to-edge Repair of Congenital Familiar Tricuspid Regurgitation: Case Report," J. Heart Valve Dis., 9:641-643 (2000).
Mccarthy et al., "Partial left ventriculectomy and mitral valve repair for end-stage congestive heart failure," European Journal of Cardio-thoracic Surgery, 13:337-343 (1998).
Mccarthy et al, Tricuspid Valve Repair with the Cosgrove-Edwards Annuloplasty System, Ann. Thorac. Surg., Jan. 16, 1997, pp. 267-268, vol. 64.
Moainie et al., "Correction of Traumatic Tricuspid Regurgitation Using the Double Orifice Technique," Annals of Thoracic Surgery, 73:963-965 (2002).
Morales et al., "Development of an Off Bypass Mitral Valve Repair," The Heart Surgery Forum #1999-4693, 2(2):115-120 (1999).
Nakanishi et al., "Early Outcome with the Alfieri Mitral Valve Repair," J. Cardiol., 37: 263-266 (2001) [Abstract in English; Article in Japanese].
Nielsen et al., "Edge-to-Edge Mitral Repair: Tension of the Approximating Suture and Leaflet Deformation During Acute Ischemic Mitral Regurgitation in the Ovine Heart," Circulation, 104(Suppl. I):I-29-I-35 (2001).
Noera et al., "Tricuspid Valve Incompetence Caused by Nonpenetrating Thoracic Trauma", Annals of Thoracic Surgery, 51:320-322 (1991).
Osawa et al., "Partial Left Ventriculectomy in a 3-Year Old Boy with Dilated Cardiomyopathy," Japanese Journal of Thoracic and Cardiovascular Surg, 48:590-593 (2000).
Park et al, Clinical Use of Blade Atrial Septostomy, Circulation, 1978, pp. 600-608, vol. 58.
Patel et al., #57 Epicardial Atrial Defibrillation: Novel Treatment of Postoperative Atrial Fibrillation, 2003 STS Presentation, [Abstract Only].
Privitera et al., "Alfieri Mitral Valve Repair: Clinical Outcome and Pathology," Circulation, 106:e173-e174 (2002).
Redaelli et al., "A Computational Study of the Hemodynamics After 'Edge-To-Edge' Mitral Valve Repair," Journal of Biomechanical Engineering, 123:565-570 (2001).
Reul et al., "Mitral Valve Reconstruction for Mitral Insufficiency," Progress in Cardiovascular Diseases, XXXIX(6):567-599 (1997).
Ricchi et al, Linear Segmental Annuloplasty for Mitral Valve Repair, Ann. Thorac. Surg., Jan. 7, 1997, pp. 1805-1806, vol. 63.
Robicsek et al., #60 The Bicuspid Aortic Valve: How Does It Function? Why Does It Fail? 2003 STS Presentation, [Abstract Only].

Supplemental European Search Report of EP Application No. 02746781, dated May 13, 2008, 3 total pages.
Supplementary European Search Report issued in European Application No. 05753261.6 dated Jun. 9, 2011, 3 pages total.
Tager et al, Long-Term Follow-Up of Rheumatic Patients Undergoing Left-Sided Valve Replacement With Tricuspid Annuloplasty—Validity of Preoperative Echocardiographic Criteria in the Decision to Perform Tricuspid Annuloplasty, Am. J. Cardiol., Apr. 15, 1998, pp. 1013-1016, vol. 81.
Tamura et al., "Edge to Edge Repair for Mitral Regurgitation in a Patient with Chronic Hemodialysis: Report of a Case," Kyobu Geka. The Japanese Journal of Thoracic Surgery, 54(9):788-790 (2001).
Tibayan et al., #59 Annular Geometric Remodeling in Chronic Ischemic Mitral Regurgitation, 2003 STS Presentation, [Abstract Only].
Timek et al., "Edge-to-edge mitral repair: gradients and three-dimensional annular dynamics in vivo during inotropic stimulation," Eur J. of Cardiothoracic Surg., 19:431-437 (2001).
Timek, "Edge-to-Edge Mitral Valve Repair without Annuloplasty Ring in Acute Ischemic Mitral Regurgitation," [Abstract] Clinical Science, Abstracts from Scientific Sessions, 106(19):2281 (2002).
Totaro, "Mitral valve repair for isolated prolapse of the anterior leaflet: an 11-year follow-up," European Journal of Cardio-thoracic Surgery, 15:119-126 (1999).
Uchida et al, Percutaneous Cardiomyotomy and Valvulotomy with Angioscopic Guidance, Am. Heart J., Apr. 1991, pp. 1221-1224, vol. 121.
Umana et al, 'Bow-Tie' Mitral Valve Repair: An Adjuvant Technique for Ischemic Mitral Regurgitation, Ann. Thorac. Surg., May 12, 1998, pp. 1640-1646, vol. 66.
Umana et al., "'Bow-tie' Mitral Valve Repair Successfully Addresses Subvalvular Dysfunction in Ischemic Mitral Regurgitation," Surgical Forum, XLVIII:279-280 (1997).
Votta et al., "3-D Computational Analysis of the Stress Distribution on the Leaflets after Edge-to-Edge Repair of Mitral Regurgitation," Journal of Heart Valve Disease, 11:810-822 (2002).
U.S. Appl. No. 14/577,852, Oct. 20, 2016, Office Action.
U.S. Appl. No. 14/577,852, May 16, 2017, Office Action.
U.S. Appl. No. 14/577,852, Sep. 7, 2017, Office Action.
U.S. Appl. No. 14/577,852, Apr. 25, 2018, Notice of Allowance.
U.S. Appl. No. 14/677,294, Nov. 17, 2017, Office Action.
U.S. Appl. No. 14/677,294, May 23, 2018, Notice of Allowance.
U.S. Appl. No. 14/677,294, Sep. 25, 2018, Notice of Allowance.
U.S. Appl. No. 14/805,275, Jan. 10, 2018, Office Action.
U.S. Appl. No. 60/128,690, filed Apr. 9, 1999, Deem, et al.
Arthur C. Beall et al., Clinical Experience with a Dacron Velour-Covered Teflon-Disc Mitral Valve Prosthesis, 5 Ann. Thorac. Surg. 402-10 (1968).
C. Fucci et al., Improved Results with Mitral Valve Repair Using New Surgical Techniques, 9 Eur. J. Cardiothorac. Surg. 621-27 (1995).
F. Maisano et al., The Edge-to-Edge Technique: A Simplified Method to Correct Mitral Insufficiency, 13 J. Cardio-thoracic Surgery 240-46 (1998).
Gregg W. Stone et al., Clinical Trial Design Principles and Endpoint Definitions for Transcatheter Mitral Valve Repair and Replacement: Part 1: Clinical Trial Design Principles: A Consensus Document from the Mitral Valve Academic Research Consortium, 66 J. Am. Coll. Cardiol. 278-307 (2015).
Juan P. Umaña et al., "Bow-Tie" Mitral Valve Repair: An Adjuvant Technique for Ischemic Mitral Regurgitation, 66 Annals of Thoracic Surgery 1640-46 (1998).
Netter, F. H., et al., "The Ciba Collection of Medical Illustrations," vol. 5. Royal Victorian Institute for the Blind Tertiary Resource Service, Melbourne (1969).
Randas J. V. Batista et al., Partial Left Ventriculectomy to Treat End-Stage Heart Disease, 64 Ann. Thorac. Surg. 634-38 (1997).
Ross M. Reul et al., Mitral Valve Reconstruction for Mitral Insufficiency, 39 Progress in Cardiovascular Diseases 567-99 (1997).
Derwent citing German language patent, EP 684012 published Nov. 12, 1995, for: "Thread for constructing surgical seam—has flexible

(56) References Cited

OTHER PUBLICATIONS section with two ends, with lower fastening part on thread first end having hollow cylinder with continuous hole through which surgical needle threads".
Vismara et al., "Transcatheter Edge-to-Edge Treatment of Functional Tricuspid Regurgitation in an Ex Vivo Pulsatile Heart Model," JACC 68(10):1024-1033 (2016).
U.S. Appl. No. 60/051,078, filed Jun. 27, 1997, Oz, et al.
Alfieri, O., et al., "Novel Suture Device for Beating-Heart Mitral Leaflet Approximation," Ann Thorac Surg 74:1488-93 (2002).
Alfieri, O., et al., "The Double-orifice Technique in Mitral Valve Repair: A Simple Solution for Complex Problems," Journal of Thoracic and Cardiovascular Surgery 122(4): 674-681 (2001).
Cribier, A., et al., "Percutaneous Mitral Valvotomy with a Metal Dilatator," The Lancet 349:1667 (1997).
Feldman, T., et al., "Technique of Percutaneous Transvenous Mitral Commissurotomy Using the Inoue Balloon Catheter," Catheterization and Cardiovascular Diagnosis Supplement 2:26-34 (1994).
Glazier, J. and Turi, Z., "Percutaneous Balloon Mitral Valvuloplasty," Progress in Cardiovascular Diseases 40(1):5-26 (1997).
Hung et al., "Atrial Septal Puncture Technique in Percutaneous Transvenous Mitral Commissurotomy : Mitral Valvuloplasty Using the Inoue Balloon Catheter Technique," Catheterization and Cardiovascular Diagnosis 26: 275-284 (1992).
Hung et al., "Pitfalls and Tips in Inoue Balloon Mitral Commissurotomy," Catheterization and Cardiovascular Diagnosis, 37:188-199 (1996).
Inoue, K. and Feldman, T., "Percutaneous Transvenous Mitral Commissurotomy Using the Inoue Balloon Catheter," Catheterization and Cardiovascular Diagnosis 28:119-125 (1993).
Inoue, K., et al., "Clinical Application of Transvenous Mitral Commissurotomy by a New Balloon Catheter," J Thorac Cardiovasc Surg 87:394-402 (1984).
Lau, K. and Hung, J., "'Balloon Impasse'; A Marker for Severe Mitral Subvalvular Disease and a Predictor of Mitral Regurgitation in Inoue-Balloon Percutaneous Transvenous Mitral Commissurotomy," Catheterization and Cardiovascular Diagnosis 35:310-319 (1995).
Lock et al., "Transcatheter Closure of Atrial Septal Defects: Experimental Studies," Circulation 79:1091-1099 (1989).
McCarthy, P., et al., "Early Results with Partial Left Ventriculectomy," J Thorac Cardiovasc Surg 114(5):755-765 (1997).
Morales et al., "Development of an Off Bypass Mitral Valve Repair," The Heart Surgery Forum, 2(2):115-120 (1999).
O'Rourke, R. and Crawford, M., "Mitral Valve Regurgitation," Year Book Medical Publishers, Inc. 1-52 (1984).
Otto, Catherine M., "Timing of Surgery in Mitral Regurgitation," Heart 89:100-105 (2003).
Werker, P. and Kon M., "Review of Facilitated Approaches to Vascular Anastomosis Surgery," Ann Thorac Surg 63:122-7 (1997).
Abe et al., "Updated: De Vega's Annuloplasty for Acquired Tricuspid Disease: Early and Late Results in 110 Patients," Ann. Thorac. Surg. 62:1876-1877 (1996).
Alfieri et al., "The Edge to Edge Technique," The European Association for Cardio-Thoracic Surgery, 14th Annual Meeting, Frankfurt / Germany, Oct. 7-11, 2000, Post Graduate Courses, Book of Proceedings.
Bhudia et al., "Edge-to-edge Mitral Repair: A Versatile Mitral Repair," http://www.sts.org/doc/7007 accessed on Sep. 24, 2008.
Bolling et al., "Surgery for Acquired Heart Disease: Early Outcome of Mitral Valve Reconstruction in Patients with End-stage Cardiomyopathy," J. Thor. And Cardiovasc. Surg., Apr. 1995, pp. 676-683, vol. 109.
Chinese Office Action dated Sep. 9, 2013 in Application No. 200980158707.2 (with English translation).
Derwent citing Japanese language patent, JP 11089937 published Jun. 4, 1999, for: "Catheter for mitral regurgitation test—includes jet nozzles provided on rear side of large diametered spindle shaped portion attached to end of narrow diametered tube".
Extended European Search Report dated Jul. 19, 2018 in EP 18177999.2.
Frazier et al., "Early Clinical Experience with an Implantable, Intracardiac Circulatory Support Device: Operative Considerations and Physiologic Implications," http://www.sts.org/doc/7007 accessed on Sep. 24, 2008.
Gateliene et al., "Early and late postoperative results of mitral and tricuspid valve insufficiency surgical treatment using edge-to-edge central coaptation procedure," Medicina (Kaunas) 38(Suppl. 2):172-175 (2002).
Gundry et al., "Facile Mitral Valve Repair Utilizing Leaflet Edge Approximation: Midterm Results of the Alfieri Figure of Eight Repair," The Western Thoracic Surgical Association, Scientific Session (May 1999).
Gupta et al., "Influence of Older Donor Grafts on Heart Transplant Survival: Lack of Recipient Effects," http://www.sts.org/doc/7007 accessed on Sep. 24, 2008.
Khan et al., "Blade Atrial Septostomy: Experience with the First 50 Procedures," Cathet. Cardiovasc. Diagn., Aug. 1991, pp. 257-262, vol. 23.
Maisano et al., "The Double Orifice Repair for Barlow Disease: A Simple Solution for Complex Repair," Circulation 100(18)I-94 (1999).
Patel et al., "Epicardial Atrial Defibrillation: Novel Treatment of Postoperative Atrial Fibrillation," http://www.sts.org/doc/7007 accessed on Sep. 23, 2008.
Robicsek et al., "The Bicuspid Aortic Valve. How Does It Function? Why Does It Fail," http://www.sts.org/doc/7007 accessed on Sep. 24, 2008.
Supplemental European Search Report of EP Application No. 02746781, dated May 13, 2008, 3 pages total.
Tibayan et al., "Annular Geometric Remodeling in Chronic Ischemic Mitral Regurgitation," http://www.sts.org/doc/7007 accessed on Sep. 24, 2008.
Extended European Search Report dated Nov. 18, 2020 in Application No. EP 20177502.

\* cited by examiner

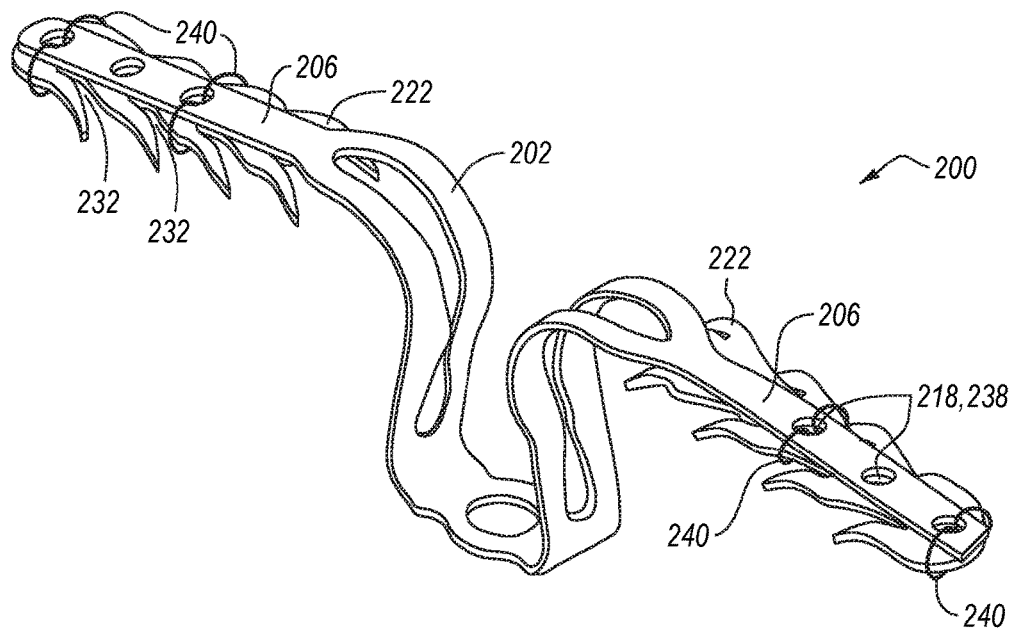
FIG. 10A
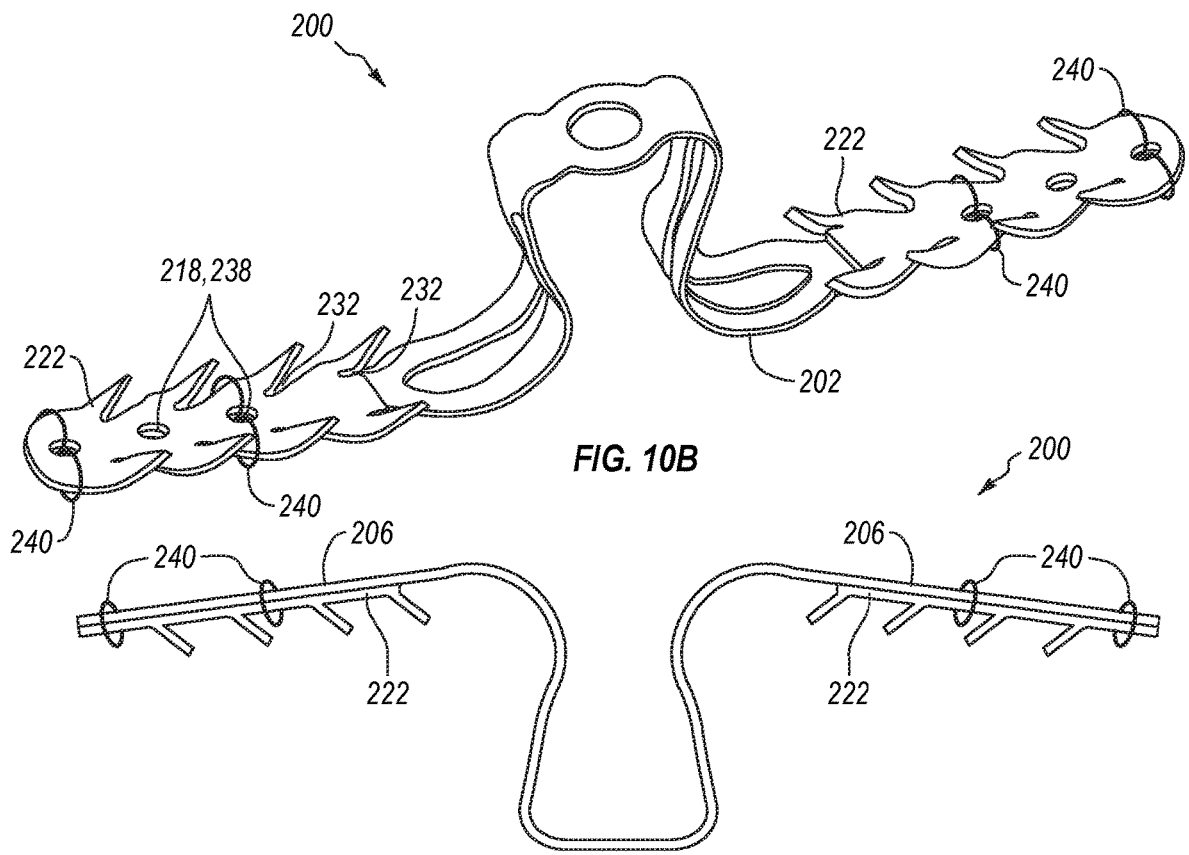
FIG. 10B
FIG. 10C

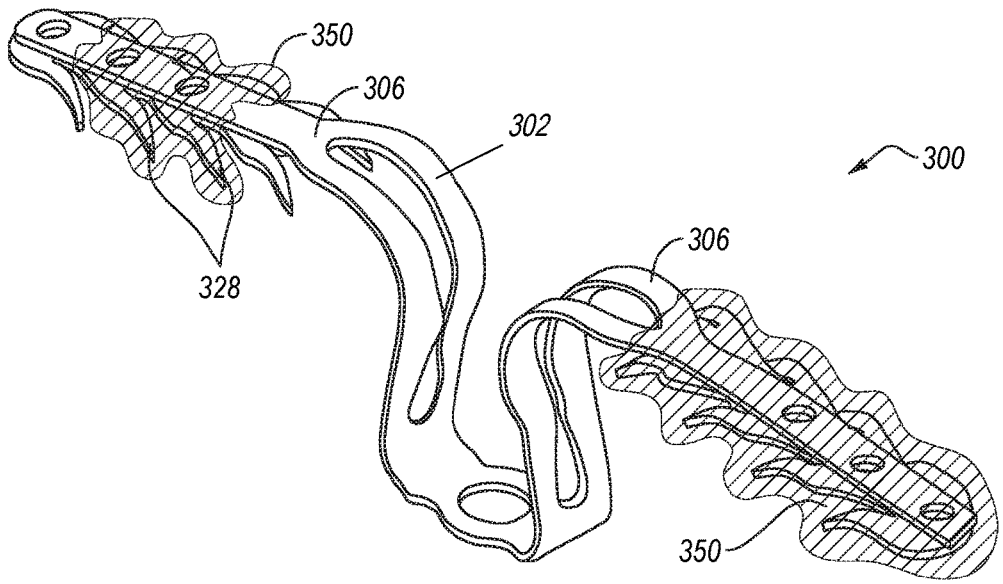
FIG. 11A
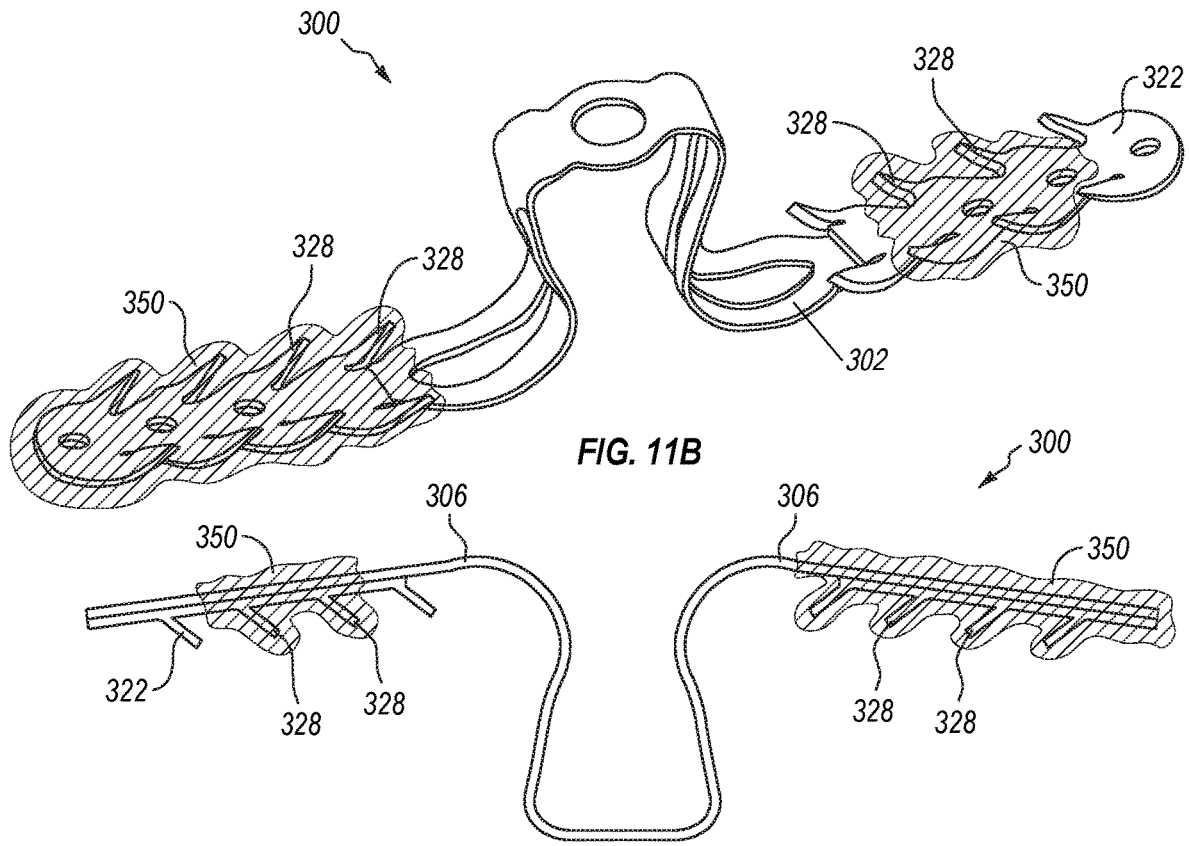
FIG. 11B
FIG. 11C

TISSUE FIXATION DEVICES AND METHODS

CROSS-REFERENCE TO RELATED APPLICATIONS

This application is a continuation of U.S. patent application Ser. No. 14/677,294, filed Apr. 2, 2015, now U.S. Pat. No. 10,524,912, the entire contents of which are incorporated by reference herein.

BACKGROUND

The present invention relates generally to medical methods, devices, and systems. In particular, the present invention relates to methods, devices, and systems for the endovascular, percutaneous or minimally invasive surgical treatment of bodily tissues, such as tissue approximation or valve repair. More particularly, the present invention relates to repair of valves of the heart and venous valves, and devices and methods for removing or disabling mitral valve repair components through minimally invasive procedures.

Surgical repair of bodily tissues often involves tissue approximation and fastening of such tissues in the approximated arrangement. When repairing valves, tissue approximation often includes coapting the leaflets of the valves in a therapeutic arrangement which may then be maintained by fastening or fixing the leaflets. Such fixation of the leaflets can be used to treat regurgitation which most commonly occurs in the mitral valve.

Mitral valve regurgitation is characterized by retrograde flow from the left ventricle of a heart through an incompetent mitral valve into the left atrium. During a normal cycle of heart contraction (systole), the mitral valve acts as a check valve to prevent flow of oxygenated blood back into the left atrium. In this way, the oxygenated blood is pumped into the aorta through the aortic valve. Regurgitation of the valve can significantly decrease the pumping efficiency of the heart, placing the patient at risk of severe, progressive heart failure.

Mitral valve regurgitation can result from a number of different mechanical defects in the mitral valve or the left ventricular wall. The valve leaflets, the valve chordae which connect the leaflets to the papillary muscles, the papillary muscles themselves, or the left ventricular wall may be damaged or otherwise dysfunctional. Commonly, the valve annulus may be damaged, dilated, or weakened, limiting the ability of the mitral valve to close adequately against the high pressures of the left ventricle during systole.

The most common treatments for mitral valve regurgitation rely on valve replacement or repair including leaflet and annulus remodeling, the latter generally referred to as valve annuloplasty. One technique for mitral valve repair which relies on suturing adjacent segments of the opposed valve leaflets together is referred to as the "bow-tie" or "edge-to-edge" technique. While all these techniques can be effective, they usually rely on open heart surgery where the patient's chest is opened, typically via a sternotomy, and the patient placed on cardiopulmonary bypass. The need to both open the chest and place the patient on bypass is traumatic and has associated high mortality and morbidity.

In some patients, a fixation device can be installed into the heart using minimally invasive techniques. The fixation device can hold the adjacent segments of the opposed valve leaflets together to reduce mitral valve regurgitation. One such device used to clip the anterior and posterior leaflets of the mitral valve together is the MitraClip® fixation device, sold by Abbott Vascular, Santa Clara, Calif., USA.

These fixation devices often include clips designed to grip and hold against tissue as the clip arms are moved and positioned against the tissue at the treatment site and then closed against the tissue. Such clips are designed to continue gripping the tissue as the fixation device is closed into a final position. In order to achieve this effect, such these clips are sometimes equipped with barbs or hooks to grip the tissue as the clip is flexed into position against the tissue.

However, some tissue fixation treatments require a fixation device to move through a wide range of grasping angles in order to be properly positioned relative to the target tissue and then to grasp the tissue and bring it to a closed position. This moving and plastically deforming components of the fixation device during positioning and closure of the device can lead to the weakening and pre-mature degradation of the fixation device. Additionally, some tissue fixation treatments require that the fixation device maintain a degree of flexibility and mobility to allow a range of physiological movement even after the device has been properly placed and the target tissue has been properly fixed into the desired position, This can increase the risk of pre-mature failure of the device as continued plastic deformation of the flexing components (e.g., from the continuous opening and closing of valve leaflets) leads to unfavorable degradation of the device.

For these reasons, there is an ongoing need to provide alternative and additional methods, devices, and systems for tissue fixation that provide beneficial elasticity and durability of the flexing components without unduly increasing the associated manufacturing costs of the flexing components. There is also a need to provide such methods, devices, and systems in a manner that does not limit the tissue gripping ability of the tissue fixation device. At least some of the embodiments disclosed below are directed toward these objectives.

DESCRIPTION OF THE BACKGROUND ART

Minimally invasive and percutaneous techniques for coapting and modifying mitral valve leaflets to treat mitral valve regurgitation are described in PCT Publication Nos. WO 98/35638; WO 99/00059; WO 99/01377; and WO 00/03759; WO 2000/060995; WO 2004/103162. Maisano et al. (1998) Eur. J. Cardiothorac. Surg. 13:240-246; Fucci et al. (1995) Eur. J. Cardiothorac. Surg. 9:621-627; and Umana et al. (1998) Ann. Thorac. Surg. 66:1640-1646, describe open surgical procedures for performing "edge-to-edge" or "bow-tie" mitral valve repair where edges of the opposed valve leaflets are sutured together to lessen regurgitation. Dec and Fuster (1994) N. Engl. J. Med. 331:1564-1575 and Alvarez et al. (1996) J. Thorac. Cardiovasc. Surg. 112:238-247 are review articles discussing the nature of and treatments for dilated cardiomyopathy.

Mitral valve annuloplasty is described in the following publications: Bach and Bolling (1996) Am. J. Cardiol. 78:966-969; Kameda et al. (1996) Ann. Thorac. Surg. 61:1829-1832; Bach and Bolling (1995) Am. Heart J. 129: 1165-1170; and Bolling et al. (1995) 109:676-683. Linear segmental annuloplasty for mitral valve repair is described in Ricchi et al. (1997) Ann. Thorac. Surg. 63:1805-1806. Tricuspid valve annuloplasty is described in McCarthy and Cosgrove (1997) Ann. Thorac. Surg. 64:267-268; Tager et al. (1998) Am. J. Cardiol. 81:1013-1016; and Abe et al. (1989) Ann. Thorac. Surg. 48:670-676.

Percutaneous transluminal cardiac repair procedures are described in Park et al. (1978) Circulation 58:600-608; Uchida et al. (1991) Am. Heart J. 121: 1221-1224; and Ali Khan et al. (1991) Cathet. Cardiovasc. Diagn. 23:257-262. Endovascular cardiac valve replacement is described in U.S. Pat. Nos. 5,840,081; 5,411,552; 5,554,185; 5,332,402; 4,994,077; and 4,056,854. U.S. Pat. No. 3,671,979 describes a catheter for temporary placement of an artificial heart valve.

Other percutaneous and endovascular cardiac repair procedures are described in U.S. Pat. Nos. 4,917,089; 4,484,579; and 3,874,338; and PCT Publication No. WO 91/01689.

Thoracoscopic and other minimally invasive heart valve repair and replacement procedures are described in U.S. Pat. Nos. 5,855,614; 5,829,447; 5,823,956; 5,797,960; 5,769,812; and 5,718,725.

BRIEF SUMMARY

The present disclosure describes methods and devices for gripping tissue in a tissue repair and/or fixation procedure, such as in a mitral valve repair procedure. Certain embodiments of a tissue gripping device include a flexible member formed from a shape-memory material, the flexible member comprising a base section and an arm, the arm having a first end connected to the base section, a free end extending away from the base section, and an attachment surface disposed between the joining end and the free end, and at least one tissue gripping member formed from a second material, the second material being more rigid than the shape-memory material, the tissue gripping member comprising a mating surface coupled to the attachment surface of the arm to join the tissue gripping member to the flexible member, and a tissue gripping surface disposed opposite the mating surface, the tissue gripping surface including a frictional element configured to resist movement of tissue away from the tissue gripping surface after the tissue has contacted the tissue gripping surface.

Certain embodiments of a tissue fixation system configured for intravascular delivery and for use in joining mitral valve tissue for treatment of the mitral valve include: a body; a proximal element comprising a flexible member formed from a shape-memory material, the flexible member comprising a base section and an arm, the arm having a first end connected to the base section, a free end extending away from the base section, and an attachment surface disposed between the joining end and the free end, and at least one tissue gripping member formed from a second material, the second material being more rigid than the shape-memory material, the tissue gripping member comprising a mating surface coupled to the attachment surface of the arm to join the tissue gripping member to the flexible member, and a tissue gripping surface disposed opposite the mating surface, the tissue gripping surface including a frictional element configured to resist movement of tissue away from the tissue gripping surface after the tissue has contacted the tissue gripping surface; and a distal element having a first end pivotally coupled to the body and extending to a free second end and a tissue engagement surface between the first and second end, the tissue engagement surface being configured to approximate and engage a portion of the leaflets of the mitral valve, wherein the proximal element is configured to cooperate with the distal element to form a space for receiving a portion of mitral valve tissue therebetween.

Certain embodiments of a method of manufacturing a tissue gripping device of the present disclosure include: forming a flexible member from a shape-memory alloy by cutting a pattern shape and heat shape setting at least one bend feature, the flexible member comprising a base section and an arm, the arm having a first end connected to the base section, a free end extending away from the base section, and an attachment surface disposed between the joining end and the free end, the at least one bend feature being disposed between the first end and the free end of the arm; forming a tissue gripping member from a second material by die stamping the second material to form a plurality of raised barbs and a plurality of slotted recesses along the side edge of the tissue gripping member, the second material being more rigid than the shape-memory material, the tissue gripping member comprising a mating surface and a tissue gripping surface disposed opposite the mating surface; and attaching the tissue gripping member to the flexible member by coupling the mating surface of the tissue gripping member to the attachment surface of the arm.

Certain embodiments provide advantages and benefits over tissue gripping devices, systems, and methods of the prior art. For example, providing a flexible member formed from a shape-memory material may provide superelasticity over the wide range of grasping angles covered during positioning of a tissue gripping device at a treatment site, such as during mitral valve leaflet grasp attempts during a mitral valve repair procedure. Additionally, avoiding plastic deformation of the flexible member during positioning and/or during post-implanting movement can increase the function and/or life of the device. Furthermore, embodiments providing one or more tissue gripping members formed from a second material can provide easier and more cost-effective manufacturing of tissue gripping frictional elements and other features of the tissue gripping member(s) as opposed to forming them using a shape-memory material, such as by forming them directly on the flexible member. Certain embodiment may therefore provide the benefits of superelastic properties where such properties are desired, while simultaneously providing more rigidity and/or easier manufacturability where such properties are desired.

These and other objects and features of the present disclosure will become more fully apparent from the following description and appended claims, or may be learned by the practice of the embodiments of the invention as set forth hereinafter.

BRIEF DESCRIPTION OF THE DRAWINGS

To further clarify the above and other advantages and features of the present disclosure, a more particular description of the invention will be rendered by reference to specific embodiments thereof which are illustrated in the appended drawings. It is appreciated that these drawings depict only illustrated embodiments of the invention and are therefore not to be considered limiting of its scope. Embodiments of the invention will be described and explained with additional specificity and detail through the use of the accompanying drawings in which:

FIGS. 10A-10C illustrate detailed views of a proximal element of a tissue fixation device, with a plurality of tissue gripping members joined to a flexible member by suture lines; and FIGS. 11A-11C illustrate detailed views of a proximal element of a tissue fixation device, the proximal element having a cover, and a plurality of tissue gripping members held against a flexible member by the cover.

DETAILED DESCRIPTION

I. Cardiac Physiology

Figure 1:
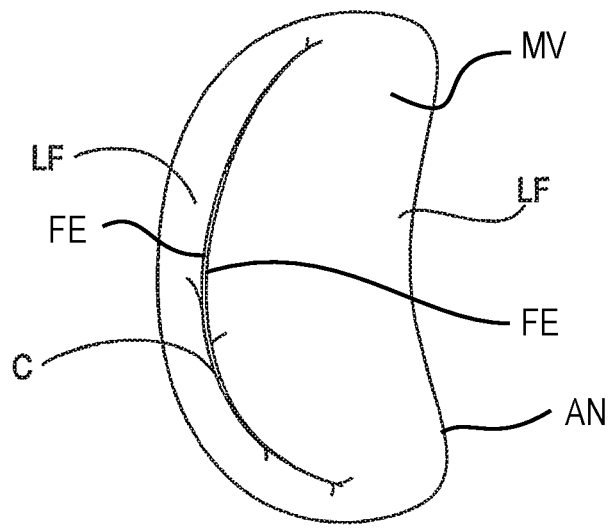
FIG. 1 illustrates free edges of leaflets of the mitral valve in normal coaptation.
Figure 2:
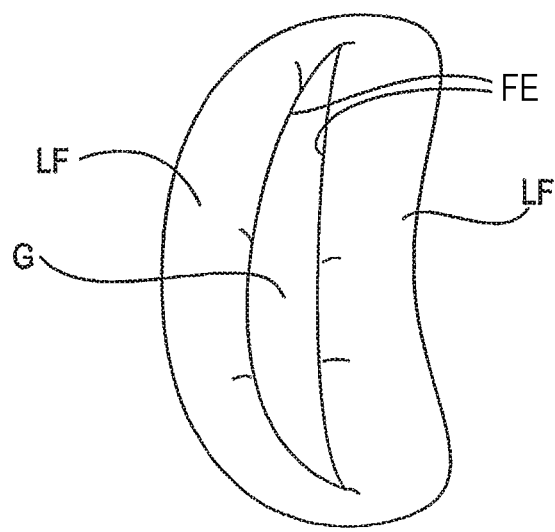
FIG. 2 illustrates the free edges in regurgitative coaptation.

As shown in FIG. 1, the mitral valve (MV) comprises a pair of leaflets (LF) having free edges (FE) which, in patients with normal heart structure and function, meet evenly to close along a line of coaption (C). The leaflets (LF) attach to the surrounding heart structure along an annular region called the annulus (AN). The free edges (FE) of the leaflets (LF) are secured to the lower portions of the left ventricle LV through chordae tendinae (or "chordae"). As the left ventricle of a heart contracts (which is called "systole"), blood flow from the left ventricle to the left atrium through the mitral valve (MV) (called "mitral regurgitation") is usually prevented by the mitral valve. Regurgitation occurs when the valve leaflets do not close properly and allow leakage from the left ventricle into the left atrium. A number of heart structural defects can cause mitral regurgitation. FIG. 2 shows a mitral valve with a defect causing regurgitation through a gap (G).

II. Overview of Mitral Valve Fixation System

Several methods for repairing or replacing a defective mitral valve exist. Some defects in the mitral valve can be treated through intravascular procedures, where interventional tools and devices are introduced and removed from the heart through the blood vessels. One method of repairing certain mitral valve defects includes intravascular delivery of a fixation device to hold portions of the mitral valve tissues in a certain position. One or more interventional catheters may be used to deliver a fixation device to the mitral valve and install it there as an implant to treat mitral regurgitation.

Figure 3A:
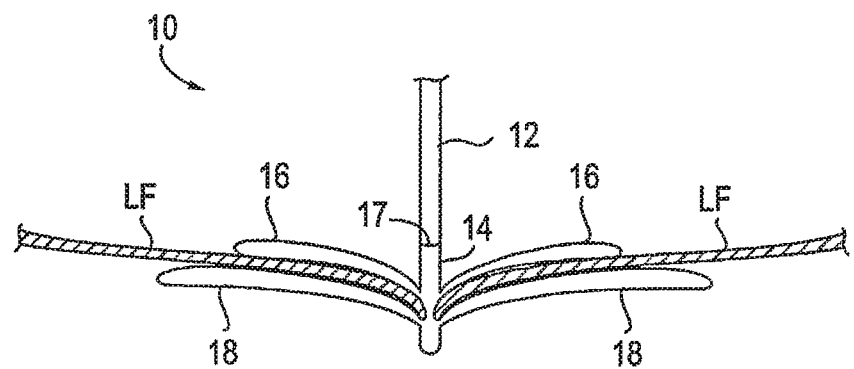
FIGS. 3A-3C illustrate grasping of the leaflets with a fixation assembly, inversion of the distal elements of the fixation assembly and removal of the fixation assembly, respectively.

FIG. 3A illustrates a schematic of an interventional tool 10 with a delivery shaft 12 and a fixation device 14. The tool 10 has approached the mitral valve MV from the atrial side and grasped the leaflets LF. The fixation device 14 is releasably attached to the shaft 12 of the interventional tool 10 at the distal end of the shaft 12. In this application, when describing devices, "proximal" means the direction toward the end of the device to be manipulated by the user outside the patient's body, and "distal" means the direction toward the working end of the device that is positioned at the treatment site and away from the user. When describing the mitral valve, proximal means the atrial side of the leaflets and distal means the ventricular side of the leaflets. The fixation device 14 comprises proximal elements 16 and distal elements 18 which protrude radially outward and are positionable on opposite sides of the leaflets LF as shown so as to capture or retain the leaflets therebetween. The fixation device 14 is coupleable to the shaft 12 by a coupling mechanism 17.

Figure 3B:
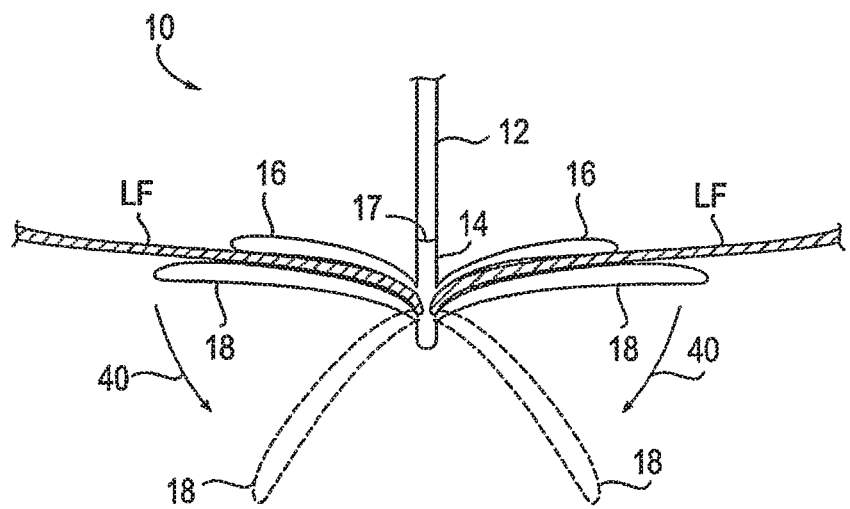
Figure 3C:
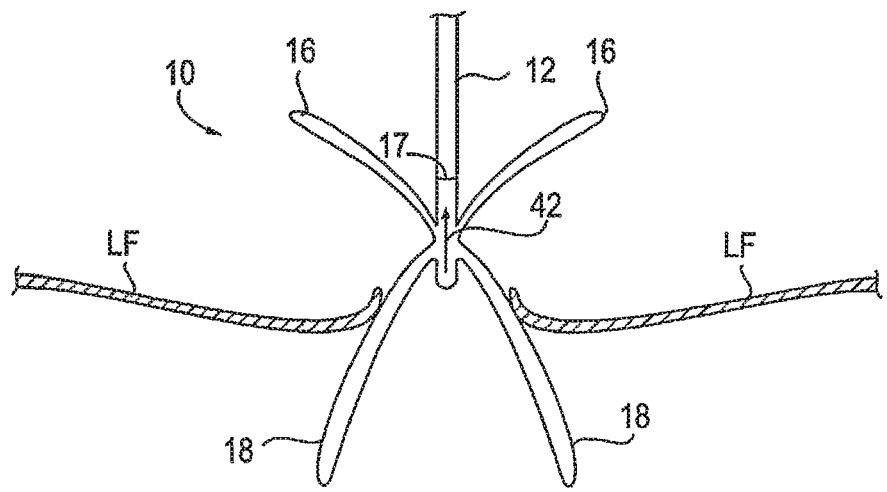

FIG. 3B illustrates that the distal elements 18 may be moved in the direction of arrows 40 to an inverted position. The proximal elements 16 may be raised as shown in FIG. 3C. In the inverted position, the device 14 may be repositioned and then be reverted to a grasping position against the leaflets as in FIG. 3A. Or, the fixation device 14 may be withdrawn (indicated by arrow 42) from the leaflets as shown in FIG. 3C. Such inversion reduces trauma to the leaflets and minimizes any entanglement of the device with surrounding tissues.

Figure 4:
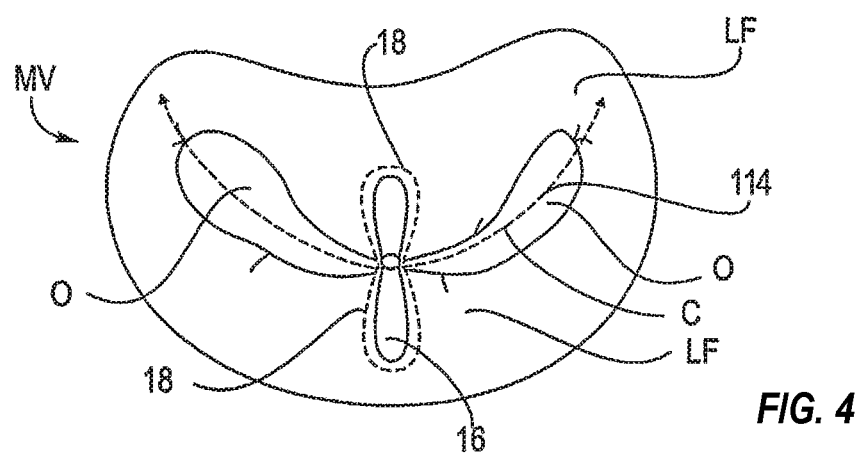
FIG. 4 illustrates the fixation assembly in a desired orientation relative to the leaflets.

FIG. 4 illustrates the fixation device 14 in a desired orientation in relation to the leaflets LF. The mitral valve MV is viewed from the atrial side, so the proximal elements 16 are shown in solid line and the distal elements 18 are shown in dashed line. The proximal and distal elements 16, 18 are positioned to be substantially perpendicular to the line of coaptation C. During diastole (when blood is flowing from the left atrium to the left ventricle), fixation device 14 holds the leaflets LF in position between the elements 16, 18 surrounded by openings or orifices O which result from the diastolic pressure gradient, as shown in FIG. 4. Once the leaflets are coapted in the desired arrangement, the fixation device 14 is detached from the shaft 12 and left behind as an implant.

Figure 5:
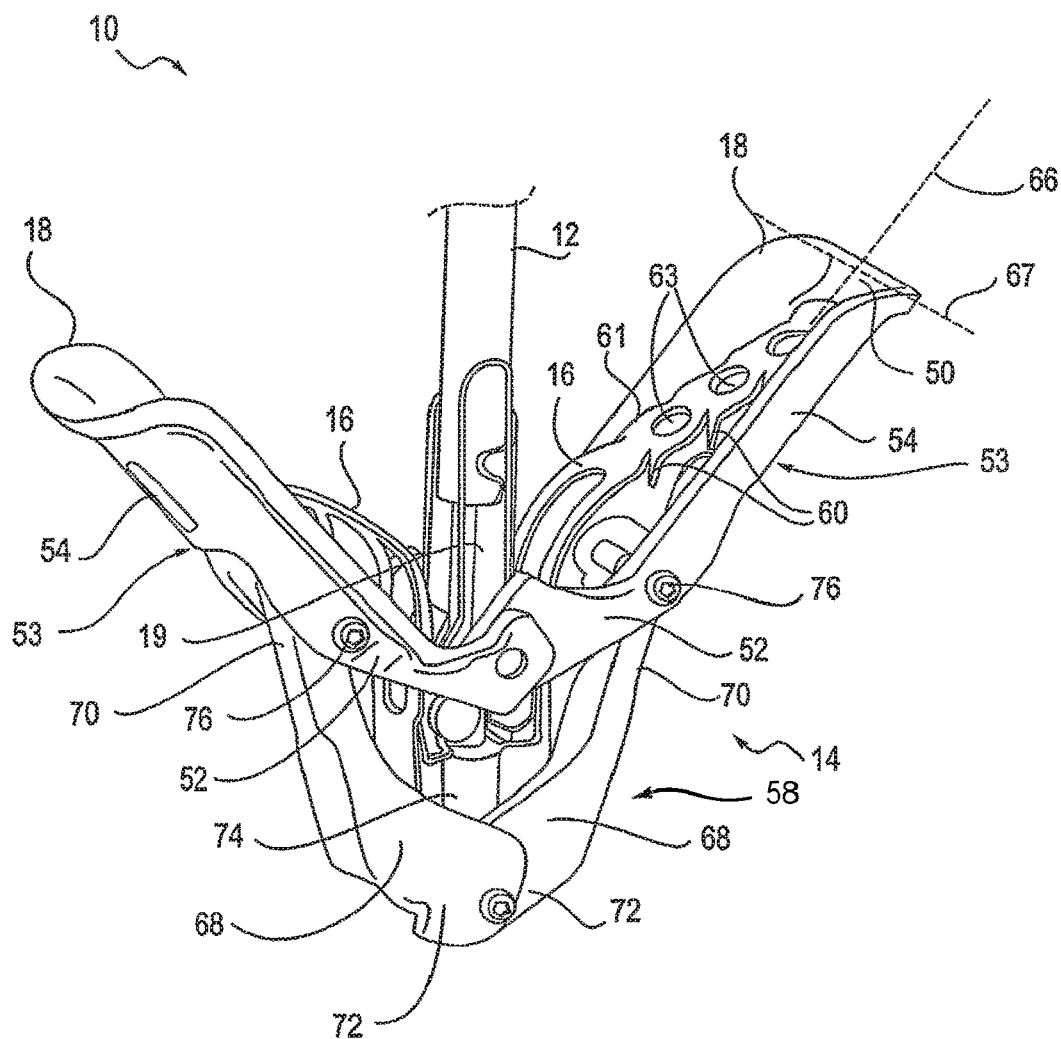
FIG. 5 illustrates an exemplary fixation assembly coupled to a shaft.

FIG. 5 illustrates an exemplary fixation device 14. The fixation device 14 is shown coupled to a shaft 12 to form an interventional tool 10. The fixation device 14 includes a coupling member 19, a pair of opposed proximal elements 16, and a pair of opposed distal elements 18. The distal elements 18 comprise elongate arms 53, each arm having a proximal end 52 rotatably connected to the coupling member 19 and a free end 54. Preferably, each free end 54 defines a curvature about two axes, axis 66 perpendicular to longitudinal axis of arms 53, and axis 67 perpendicular to axis 66 or the longitudinal axis of arms 53. Arms 53 have engagement surfaces 50. Arms 53 and engagement surfaces 50 are configured to engage about 4-10 mm of tissue, and preferably about 6-8 mm along the longitudinal axis of arms 53. Arms 53 further include a plurality of openings.

The proximal elements 16 are preferably resiliently biased toward the distal elements 18. When the fixation device 14 is in the open position, each proximal element 16 is separated from the engagement surface 50 near the proximal end 52 of arm 53 and slopes toward the engagement surface 50 near the free end 54 with the free end of the proximal element 16 contacting engagement surface 50, as illustrated in FIG. 5. Proximal elements 16 include a plurality of openings 63 and scalloped side edges 61 to increase their grip on tissue. The proximal elements 16 optionally include a frictional element or multiple frictional elements to assist in grasping the leaflets. The frictional elements may comprise barbs 60 having tapering pointed tips extending toward engagement surfaces 50. Any suitable frictional elements may be used, such as prongs, windings, bands, barbs, grooves, channels, bumps, surface roughening, sintering, high-friction pads, coverings, coatings or a combination of these. The proximal elements 16 may be covered with a fabric or other flexible material. Preferably, when fabrics or coverings are used in combination with barbs or other frictional features, such features will protrude through such fabric or other covering so as to contact any tissue engaged by proximal elements 16.

The fixation device 14 also includes an actuator or actuation mechanism 58. The actuation mechanism 58 comprises two link members or legs 68, each leg 68 having a first end 70 which is rotatably joined with one of the distal elements 18 at a riveted joint 76 and a second end 72 which is rotatably joined with a stud 74. The actuation mechanism 58 comprises two legs 68 which are each movably coupled to a base 69. Or, each leg 68 may be individually attached to the stud 74 by a separate rivet or pin. The stud 74 is joinable with an actuator rod which extends through the shaft 12 and is axially extendable and retractable to move the stud 74 and therefore the legs 68 which rotate the distal elements 18 between closed, open and inverted positions. Immobilization of the stud 74 holds the legs 68 in place and therefore holds the distal elements 18 in a desired position. The stud 74 may also be locked in place by a locking feature. This actuator rod and stud assembly may be considered a first means for selectively moving the distal elements between a first position in which the distal elements are in a collapsed, low profile configuration for delivery of the device, a second position in which the distal elements are in an expanded configuration for positioning the device relative to the mitral valve, and a third position in which the distal elements are secured in position against a portion of the leaflets adjacent the mitral valve on the ventricular side.

Figure 6A:
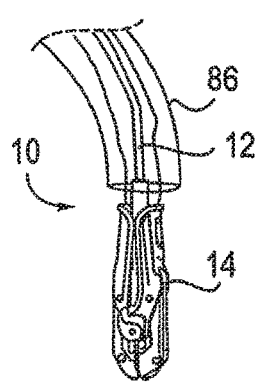
FIGS. 6A-6B, 7A-7C, and 8 illustrate a fixation assembly in various possible positions during introduction and placement of the assembly within the body to perform a therapeutic procedure.

FIGS. 6A-6B, 7A-7C, and 8 illustrate various possible positions of the fixation device 14 of FIG. 5. FIG. 6A illustrates an interventional tool 10 delivered through a catheter 86. The catheter 86 may take the form of a guide catheter or sheath. The interventional tool 10 comprises a fixation device 14 coupled to a shaft 12 and the fixation device 14 is shown in the closed position.

Figure 6B:
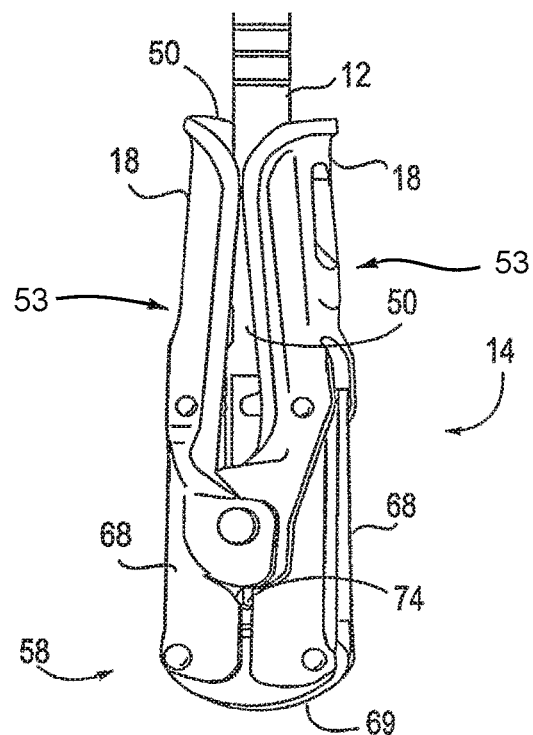

FIG. 6B illustrates a device similar to the device of FIG. 6A in a larger view. In the closed position, the opposed pair of distal elements 18 are positioned so that the engagement surfaces 50 face each other. Each distal element 18 comprises an elongate arm 53 having a cupped or concave shape so that together the arms 53 surround the shaft 12. This provides a low profile for the fixation device 14.

Figure 7A:
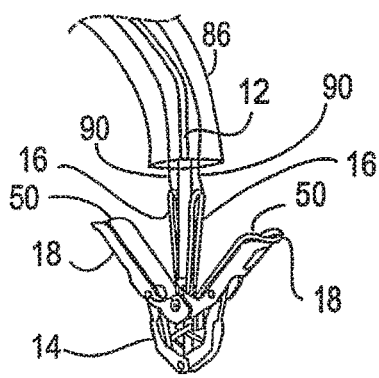
Figure 7B:
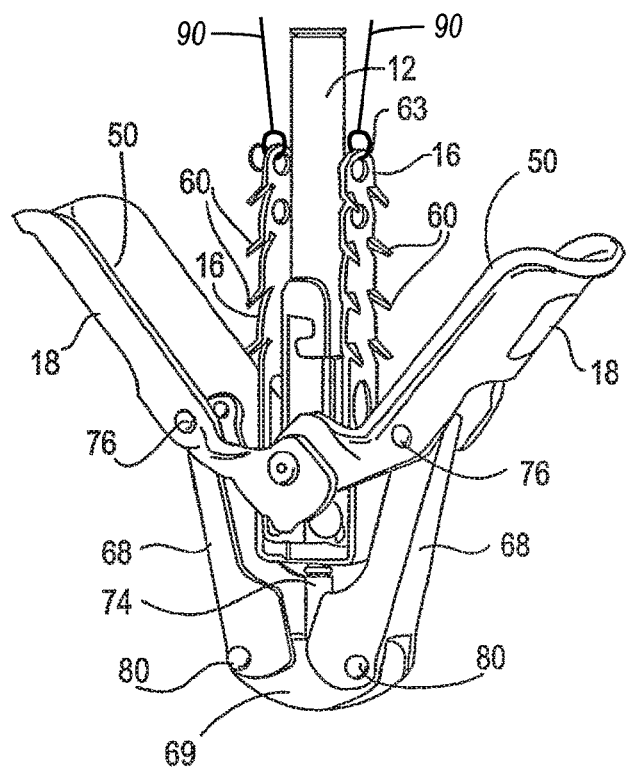

FIGS. 7A-7B illustrate the fixation device 14 in the open position. In the open position, the distal elements 18 are rotated so that the engagement surfaces 50 face a first direction. Distal advancement of the actuator rod relative to shaft 12, and thus distal advancement of the stud 74 relative to coupling member 19, applies force to the distal elements 18 which begin to rotate around joints 76. Such rotation and movement of the distal elements 18 radially outward causes rotation of the legs 68 about joints 80 so that the legs 68 are directed slightly outwards. The stud 74 may be advanced to any desired distance correlating to a desired separation of the distal elements 18. In the open position, engagement surfaces 50 are disposed at an acute angle relative to shaft 12, and are preferably at an angle of between 90 and 180 degrees relative to each other. In the open position, the free ends 54 of arms 53 may have a span therebetween of about 10-20 mm, usually about 12-18 mm, and preferably about 14-16 mm.

Figure 7C:
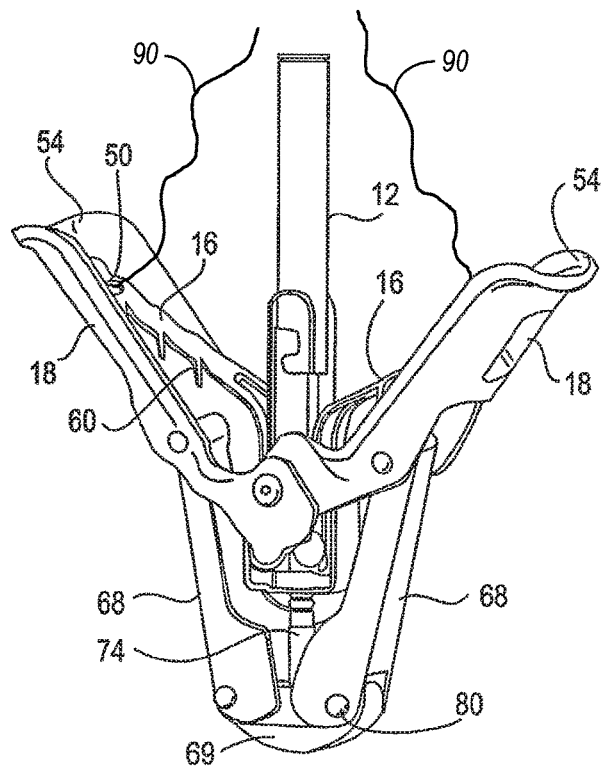

Proximal elements 16 are typically biased outwardly toward arms 53. The proximal elements 16 may be moved inwardly toward the shaft 12 and held against the shaft 12 with the aid of proximal element lines 90 which can be in the form of sutures, wires, nitinol wire, rods, cables, polymeric lines, or other suitable structures. The proximal element lines 90 extend through the shaft 302 of the delivery catheter 300 and connect with the proximal elements 16. The proximal elements 16 are raised and lowered by manipulation of the proximal element lines 90. For example, FIG. 7C illustrates proximal elements 16 in a lowered position as a result of providing slack to proximal element lines 90. Once the device is properly positioned and deployed, the proximal element lines can be removed by withdrawing them through the catheter and out the proximal end of the device 10. The proximal element lines 90 may be considered a second means for selectively moving the proximal elements between a first position in which the proximal elements are in a collapsed, low profile configuration for delivery of the device and a second position in which the proximal elements are in an expanded configuration for engaging a portion of the leaflets adjacent the mitral valve on the atrial side.

In the open position, the fixation device 14 can engage the tissue which is to be approximated or treated. The interventional tool 10 is advanced through the mitral valve from the left atrium to the left ventricle. The distal elements 18 are then deployed by advancing actuator rod relative to shaft 12 to thereby reorient distal elements 18 to be perpendicular to the line of coaptation. The entire assembly is then withdrawn proximally and positioned so that the engagement surfaces 50 contact the ventricular surface of the valve leaflets, thereby engaging the left ventricle side surfaces of the leaflets. The proximal elements 16 remain on the atrial side of the valve leaflets so that the leaflets lie between the proximal and distal elements. The interventional tool 10 may be repeatedly manipulated to reposition the fixation device 14 so that the leaflets are properly contacted or grasped at a desired location. Repositioning is achieved with the fixation device in the open position. In some instances, regurgitation may also be checked while the device 14 is in the open position. If regurgitation is not satisfactorily reduced, the device may be repositioned and regurgitation checked again until the desired results are achieved.

Figure 8:
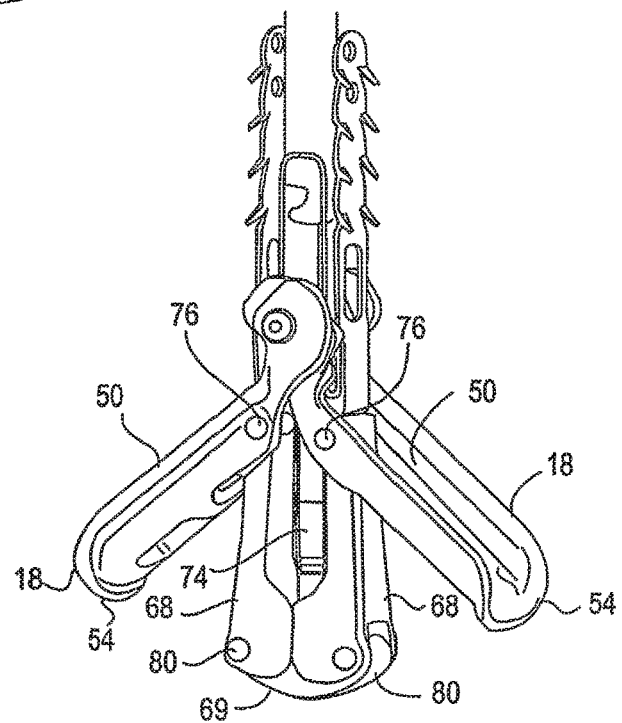

It may also be desired to invert distal elements 18 of the fixation device 14 to aid in repositioning or removal of the fixation device 14. FIG. 8 illustrates the fixation device 14 in the inverted position. By further advancement of actuator rod relative to shaft 12, and thus stud 74 relative to coupling member 19, the distal elements 18 are further rotated so that the engagement surfaces 50 face outwardly and free ends 54 point distally, with each arm 53 forming an obtuse angle relative to shaft 12.

The angle between arms 53 when the device is inverted is preferably in the range of about 270 to 360 degrees. Further advancement of the stud 74 further rotates the distal elements 18 around joints 76. This rotation and movement of the distal elements 18 radially outward causes rotation of the legs 68 about joints 80 so that the legs 68 are returned toward their initial position, generally parallel to each other. The stud 74 may be advanced to any desired distance correlating to a desired inversion of the distal elements 18. Preferably, in the fully inverted position, the span between free ends 54 is no more than about 20 mm, usually less than about 16 mm, and preferably about 12-14 mm. Barbs 60 are angled slightly in the distal direction (away from the free ends of the proximal elements 16), reducing the risk that the barbs will catch on or lacerate tissue as the fixation device is withdrawn.

Once the distal elements 18 of the fixation device 14 have been positioned in a desired location against the left ventricle side surfaces of the valve leaflets, the leaflets may then be captured between the proximal elements 16 and the distal elements 18. The proximal elements 16 are lowered toward the engagement surfaces 50 by releasing tension from proximal element lines 90, thereby releasing proximal elements 16 so that they are then free to move, in response to the internal spring bias force formed into proximal elements 16, from a constrained, collapsed position to an expanded, deployed position and so that the leaflets are held between the proximal elements 16 and the distal elements 18. If regurgitation is not sufficiently reduced, the proximal elements 16 may be raised and the distal elements 18 adjusted or inverted to reposition the fixation device 14.

After the leaflets have been captured between the proximal and distal elements 16, 18 in a desired arrangement, the distal elements 18 may be locked to hold the leaflets LF in this position or the fixation device 14 may be returned to or toward a closed position. This is achieved by retraction of the stud 74 proximally relative to coupling member 19 so that the legs 68 of the actuation mechanism 58 apply an upwards force to the distal elements 18 which in turn rotate the distal elements 18 so that the engagement surfaces 50 again face one another. The released proximal elements 16 which are biased outwardly toward distal elements 18 are concurrently urged inwardly by the distal elements 18. The fixation device 14 may then be locked to hold the leaflets in this closed position. The fixation device 14 may then be released from the shaft 12.

The fixation device 14 optionally includes a locking mechanism for locking the device 14 in a particular position, such as an open, closed or inverted position or any position therebetween. The locking mechanism may include a release harness. Applying tension to the release harness may unlock the locking mechanism. The lock lines 92 engage the release harnesses 108 of the locking mechanism 106 to lock and unlock the locking mechanism 106. The lock lines 92 extend through the shaft 302 of the delivery catheter 300. A handle attached to the proximal end of the shaft is used to manipulate and decouple the fixation device 14.

Additional disclosure regarding such fixation devices 14 may be found in PCT Publication No. WO 2004/103162 and U.S. patent application Ser. No. 14/216,787, the disclosures of both of which are incorporated herein in their entirety.

III. Improved Tissue Fixation Device

Certain embodiments of tissue fixation devices of the present disclosure include a proximal element 16 formed as a tissue gripping device as described in detail below. In some embodiments, a tissue gripping device can form the proximal element 16 of a tissue fixation device (such as any of the tissue fixation devices 14 described above with reference to FIGS. 3-8 and related discussion), and can be utilized as the proximal element 16 of the tissue fixation device. The terms "tissue gripping device" and "proximal element" or "proximal elements," as defined herein, are therefore interchangeable.

Figure 9A:
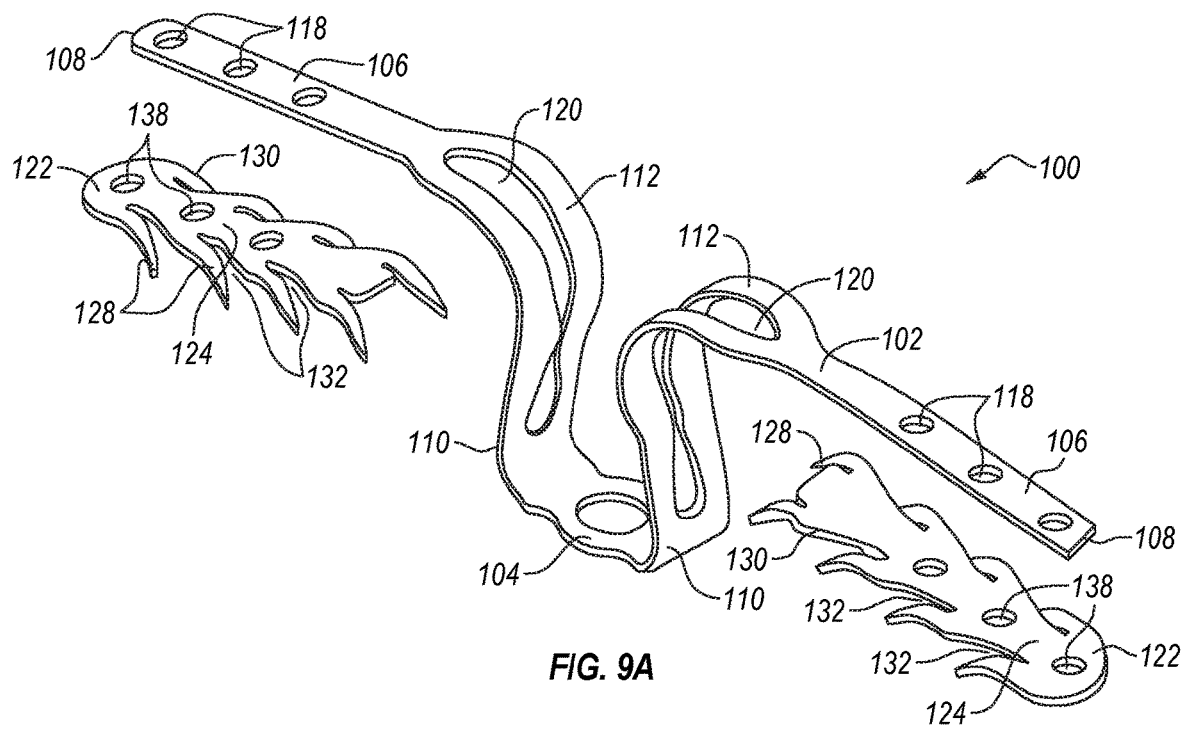
FIGS. 9A-9C illustrate detailed views of a proximal element of a tissue fixation device, the proximal element including a flexible member and a plurality of tissue gripping members.
Figure 9B:
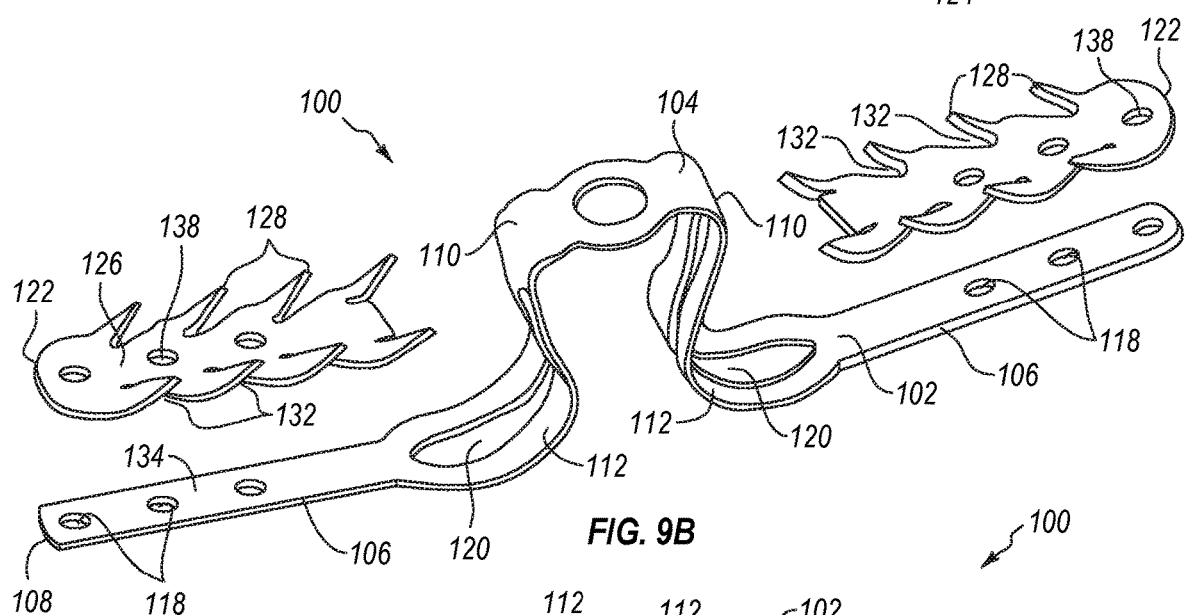
Figure 9C:
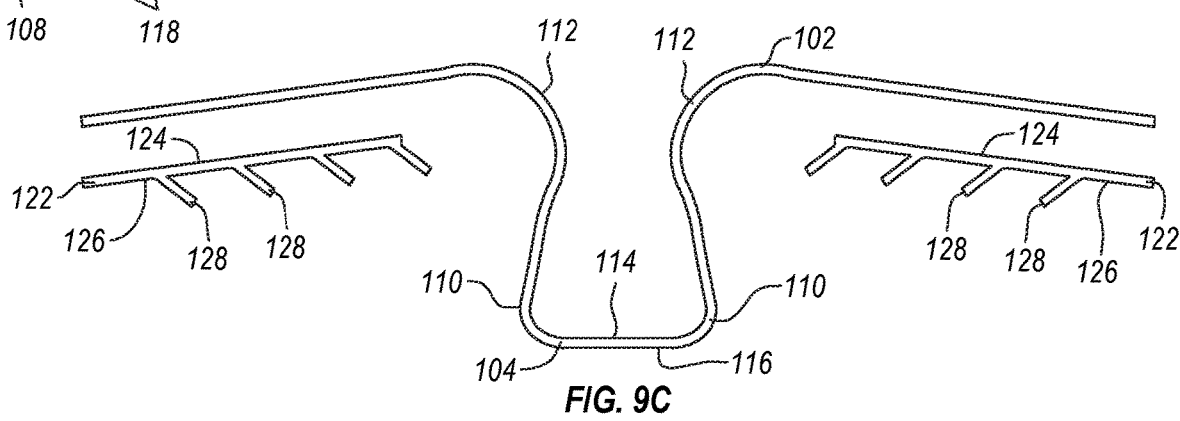

FIGS. 9A-9C illustrate an embodiment of a tissue gripping device 100 including a flexible member 102 and at least one tissue gripping member 122 (e.g., a pair of tissue gripping members 122 as illustrated) coupled to the flexible member 102. The flexible member 102 may be formed from a first material and the tissue gripping member 122 may be formed from a second, different material. In preferred embodiments, the second material has greater rigidity than the first material, making the tissue gripping member 122 more rigid than the flexible member 102. Accordingly, in such embodiments, the flexible member 102 is more flexible than the tissue gripping member 122. The flexible member 102 is preferably made from a shape-memory material such as nitinol. In this configuration, flexible member 102 exhibits superelasticity during flexing, bending, and/or otherwise positioning the tissue gripping device 100 (e.g., such as during positioning and deployment of the device at a treatment site and/or during continued movement after being deployed).

For example, during a mitral valve repair procedure, portions of the tissue gripping device may need to repeatedly pass through wide angles as multiple tissue grasping attempts are made and/or as the tissue gripping device 100 is moved into an acceptable position against the leaflets of the mitral valve. Furthermore, even after deployment against mitral valve tissue, the tissue gripping device 100 may need to provide some amount of flexibility and movement as the repaired mitral valve tissue continues to move during cardiac cycles. Forming the flexible member 102 from a shape-memory material such as nitinol avoids plastic deformation of the flexible member 102 during these movements, thereby promoting easier tissue grasping during deployment and reducing mechanical degradation of the tissue gripping device 100 from repeated and/or high levels of plastic deformation.

The tissue gripping member 122 can be formed from stainless steel or a cobalt-chromium alloy, such as a cobalt-chromium-nickel alloy or a cobalt-chromium-nickel-iron-molybdenum-manganese alloy. In preferred embodiments, the tissue gripping member 122 is formed from Elgiloy®, however, any suitable material or combinations of materials may be used. For example, a tissue gripping member 122 may be formed from a material in which frictional elements 128 (e.g., raised barbs) or other features of the tissue gripping member(s) are easily machined or otherwise formed (e.g., more easily machined relative to machining such features using a shape-memory material such as with machining frictional elements 128 directly onto the arms 106 of the flexible member 102).

The flexible member 102 includes a proximal side 114, a distal side 116, a base section 104, and a pair of arms 106, with each arm 106 extending from the base section 104 to a free end 108. In other embodiments, there may be one arm extending from a base section, or there may be more than two arms extending from a base section. For example, some embodiments may have multiple arms arrayed about a base section (e.g., in a radial fashion), and/or may include a first plurality of arms disposed opposite a second plurality of arms.

Each arm in the illustrated embodiment includes a first bend feature 110 disposed at an area adjacent to the base section 104, and a second bend feature 112 disposed a distance farther toward the free end 106 from the first bend feature 110. The first bend features 110 form angles of about 90 degrees or just under 90 degrees (e.g., about 60 to 120 degrees, about 70 to 110 degrees, or about 80 to 100 degrees) as measured from the proximal side 114, and the second bend features 112 form angles of about 90 degrees or just under 90 degrees (e.g., about 60 to 120 degrees, about 70 to 110 degrees, or about 80 to 100 degrees) as measured from the distal side 116.

The first and second bend features 110 and 112 are configured to give the flexible member 102 a bent configuration when the flexible member 102 is in a relaxed state, such that when the flexible member 102 is forced into a stressed state (e.g., by bending the flexible member 102 at one or more of the first and/or second bend features 110 and 112), the flexible member 102 is resiliently biased toward the relaxed state.

For example, an arm 106 may be deformed at the second bend feature 112 in a manner that flexes the arm 106 in a proximal direction and an inward direction, thereby flexing the arm 106 toward a straighter configuration (e.g., increasing the angle of the second bend feature 112 as measured from the distal side 116). In such a position, the flexible member 102 is in a stressed state such that the arm 106 of the flexible member 102 is resiliently biased toward a distal direction and an outward direction. Other embodiments may omit one or more of the bend features, and other embodiments may include additional bend features. These and other embodiments may include bend features with differing bend angles when in a relaxed state. For example, some embodiments may include bend features that measure greater than about 90 degrees or less than about 90 degrees when in a relaxed state.

The flexible member 102 of the illustrated embodiment includes a plurality of holes 118 distributed along the length of each arm 106. The holes 118 are configured to provide a passage or tie point for one or more sutures, wires, nitinol wires, rods, cables, polymeric lines, or other such structures. As discussed above, these materials may be coupled to one or more arms 106 to operate as proximal element lines (e.g., element lines 90 illustrated in FIGS. 7A-7C) for raising, lowering, and otherwise manipulating, positioning and/or deploying the flexible member 102. Additionally, or alternatively, the holes 118 may be configured to provide for the coupling of the flexible member 102 to one or more tissue gripping members (as discussed in detail below).

Other embodiments may include a flexible member with more or less holes and/or with holes in other positions of the flexible member. For example, some embodiments may omit holes completely, and some embodiments may include only one hole and/or only one hole per arm. Other embodiments may include holes of different shapes and/or sizes, such as holes formed as slots, slits, or other shapes. In embodiments where more than one hole is included, the holes may be uniform in size, shape, and distribution or may be non-uniform in one or more of size, shape, and distribution.

Each arm 106 of the illustrated embodiment includes a furcated section 120. The furcated section 120 may extend from the base section 104 to a position farther along the arm 106 toward the free end 108 of the arm 106, as illustrated. In other embodiments, a furcated section may be positioned at other locations along an arm and/or base section. Other embodiments may include one or more furcated sections extending completely to the free end of an arm, thereby forming a bifurcated or fork-shaped arm. Other embodiments omit any furcated sections. The furcated sections 120 of the illustrated embodiment coincide with the second bend features 112. The furcated sections 120 may be configured (e.g., in size, shape, spacing, position, etc.) so as to provide desired resiliency and/or flexibility at the coinciding second bend features 112.

The illustrated embodiment includes a pair of tissue gripping members 122, each having a mating surface 124 and a tissue gripping surface 126. Each tissue gripping member 122 includes a plurality of frictional elements 128 configured to engage with tissue at a treatment site and resist movement of tissue away from the tissue gripping member after the frictional elements 128 have engaged with the tissue. As shown in the illustrated embodiment, the frictional elements 128 are formed as angled barbs extending distally and inwardly. In this manner, tissue that is engaged with the frictional elements 128 of a tissue gripping member 122 is prevented from moving proximally and outwardly relative to the tissue gripping member 122.

The frictional elements 128 of the illustrated tissue gripping members 122 protrude from a side edge 130 of the tissue gripping members 122, thereby forming a plurality of slotted recesses 132 disposed along each side edges 130 of each tissue gripping member 122 at sections adjacent to the frictional elements 128. Other embodiments may include only one tissue gripping member or may include more than two tissue gripping members. For example, some embodiments may include multiple, separately formed tissue gripping members configured to be coupled to each arm. In other embodiments, not every arm includes a corresponding tissue gripping member. Other embodiments may include frictional elements of varying size, number, and/or shape. For example, in some embodiments the frictional elements may be formed as posts, tines, prongs, bands, grooves, channels, bumps, pads, or a combination of these or any other feature suitable for increasing friction and/or gripping of contacted tissue.

The tissue gripping members 122 of the illustrated embodiment include a plurality of holes 138 distributed along the length of each tissue gripping member 122. As with the holes 118 of the flexible member 102, the holes 138 of the tissue gripping members 122 are configured to provide a passage or tie point for one or more sutures, wires, nitinol wires, rods, cables, polymeric lines, or other such structures to operate as proximal element lines (e.g., element lines 90 illustrated in FIGS. 7A-7C) and/or to provide for the coupling of one or more of the tissue gripping members 122 to the flexible member 102.

The holes 138 of the tissue gripping member 122 of the illustrated embodiment are formed so as to coincide with the holes 118 of the flexible member 102. In this manner, the tissue gripping member 122 may be positioned relative to the flexible member 102 such that each of the holes 138 of the tissue gripping member 122 align with a corresponding hole 118 of the flexible member 102.

Other embodiments may include a tissue gripping member with more or less holes and/or with holes in other positions of the tissue gripping member. For example, some tissue gripping members may omit holes, or may include only one hole. Other embodiments may include holes of different shapes and/or sizes, such as slots, slits, or other shapes. In embodiments where more than one hole is included, the holes may be uniform in size, shape, and distribution or may be non-uniform in one or more of size, shape, and distribution. In other embodiments, not every hole of the tissue gripping member is configured to align with a corresponding hole of the flexible member and vice versa. In some embodiments, no holes are aligned when the tissue gripping member is properly positioned relative to the flexible member.

In the illustrated embodiment, the distal side of each arm 106 of the flexible member 102 includes an attachment surface 134. The tissue gripping member 122 is positioned on the distal side of the arm 106 of the flexible member 102, with the mating surface 124 of the tissue gripping member 122 facing the attachment surface 134. The tissue gripping member 122 is joined to the flexible member 102 by coupling the mating surface 124 to the attachment surface 134. In other embodiments, the mating surface and the attachment surface may be formed with corresponding press-fit portions or other locking/engaging portions configured to allow the tissue gripping member to be joined to the flexible member by engaging the corresponding press-fit portions and/or other corresponding locking portions. In some embodiments, the tissue gripping member may be fastened to the flexible member by using an adhesive or by welding, soldering, bolting, clamping, riveting, crimping or otherwise securing the tissue gripping member to the flexible member.

In some embodiments, an arm of the flexible member is configured to bend proximally while moving from a relaxed configuration toward a stressed configuration, and to resiliently flex distally toward a relaxed configuration when positioned in a stressed configuration, thereby forcing the attachment surface of the arm against the tissue gripping member as the arm flexed distally toward a relaxed configuration. For example, when a tissue gripping device is properly positioned and deployed at a mitral valve, the arm of the flexible member will operate to "sandwich" the tissue gripping member between the arm and the mitral valve tissue being gripped.

FIGS. 10A-10C illustrate an embodiment of a tissue gripping device 200 wherein the tissue gripping members 222 have been coupled to the flexible member 202. In the illustrated embodiment, each tissue gripping member 222 has been positioned next to the flexible member 202 by joining each mating surface (not shown) of each tissue gripping member 222 to one of the corresponding attachment surfaces (not shown) of the flexible member 202. In the illustrated embodiment, the tissue gripping members 222 are secured to the flexible member 202 by forming suture loops 240 through the aligned holes 218 and 238 of the flexible member 202 and the tissue gripping members 222, respectively. In this configuration, the suture loops 240 can fasten the tissue gripping member 222 to the flexible member 202 by encircling at least a portion of the tissue gripping member and at least a portion of the arm 206 of the flexible member 202 before being tied off, tightened, or otherwise secured so as to hold the tissue gripping member 222 in position against the flexible member 202.

In other embodiments, one or more suture lines may be used to tie or fasten one or more tissue gripping members to the flexible member in other configurations. For example, one or more suture lines may be threaded or laced through multiple holes on both the tissue gripping member and the flexible member before being tied off, tightened, or otherwise set in place in order to secure the tissue gripping member to the flexible member. In other embodiments, one or more suture lines do not pass through any holes. In such embodiments, suture lines may be looped or wrapped around the arm of the flexible member and the tissue gripping member to secure the tissue gripping member to the arm.

The suture line forming the suture loops 240 or other suture fastening structures may be wrapped and/or threaded a single time or multiple times before being tied, tightened, or otherwise set in place. For example, some suture lines may be wrapped repeatedly and/or may double back on themselves in order to strengthen or further secure the coupling of a tissue gripping member to an arm. In some embodiments one or more of the suture lines used to form the suture loops 240 or other suture fastening structures may also extend from the tissue gripping device 200 to act as the element lines described above (e.g., element lines 90 illustrated in FIGS. 7A-7C).

The tissue gripping members 222 of the illustrated embodiment also include a plurality of slotted recesses 232. In embodiments such as this, one or more suture loops 240 may be formed such that the suture line passes through and lodges within oppositely disposed slotted recesses 232, thereby further aiding in the securing of the tissue gripping member 222 to the arm 206 as well as promoting proper placement of the suture loop 240 and preventing slippage, loosening, or unraveling of the inner suture loop 240 from its proper position.

In other embodiments, suture loops or other suture fastening structures do not pass through or lodge within any slotted recesses. Some embodiments may include suture loops and/or suture fastening structures that pass through and/or lodge within one or more (not necessarily oppositely disposed) slotted recesses to aid in fastening the tissue gripping member to the arm of the flexible member. Yet other embodiments may include suture lines forming suture loops or other suture fastening structures that pass through and/or lodge within one or more slotted recesses but do not pass through any holes. Conversely, some embodiments may include suture lines forming suture loops or other suture fastening structures that pass through one or more holes but do not pass thorough and/or lodge within any slotted recess.

The illustrated embodiment includes two suture loops 240 at each tissue gripping member 222. In other embodiments, more or fewer suture loops or suture fastening structures may be used, though in preferred embodiments, at least two fastening points are formed (e.g., by using two or more suture loops or by threading or lacing a suture line across multiple points) in order to prevent rotational slippage of the tissue gripping member from the flexible member due to moment forces.

FIGS. 11A-11C illustrate an embodiment of a tissue gripping device 300 wherein the tissue gripping members 322 have been coupled to the flexible member 302 using at least one cover 350. The cover 350 is positioned over at least a portion of the arm 306 of the flexible member 302 and over at least a portion of the tissue gripping member 322 so as to hold the tissue gripping member 322 against the arm 306.

In preferred embodiments, the cover 350 is formed as a polymer cover which may be formed on the tissue gripping device 300 by dipping, spraying, coating or otherwise adhering it to the surfaces of the tissue gripping device 300 or to portions of the tissue gripping device 300. In some embodiments, the polymer coating may be applied to the tissue gripping member 322 and the arm 306 (or portions thereof) while the tissue gripping member 322 is held in place against the flexible member 306. The polymer coating may then cure, harden, and/or solidify to form the cover 350 and to hold the tissue gripping member 322 against the flexible member 302. In other embodiments, a polymer coating may act as an adhesive, and the polymer coating may be applied to the mating surface (not shown) and/or attachment surface (not shown) in order to adhere the tissue gripping member 322 to the arm 306 as the mating surface is positioned against the attachment surface and the polymer coating is cured.

The cover 350 may be formed in whole or in part of polyethylene terephalate, polyester, cotton, polyurethane, expanded polytetrafluoroethylene (ePTFE), silicon, or various biocompatible polymers or fibers and have any suitable form, such as a fabric, mesh, textured weave, felt, looped or porous structure. The cover 350 may also be configured to leave the frictional elements 328 (in embodiments that include them) exposed. The cover 350 may also include drugs, antibiotics, anti-thrombosis agents, or anti-platelet agents such as heparin or warfarin sodium. These agents may be impregnated in and/or coated on the cover 350 such that they are delivered to surrounding tissues and/or the blood stream when the tissue gripping device 300 is implanted into a patient.

The embodiment illustrated in FIGS. 11A-11C include some covers 350 that are positioned over the entirety of each tissue gripping member 322 and the portion of the arms 306 adjacent to each tissue gripping member 322. In other embodiments that include a cover, the cover may be positioned to cover more of the tissue gripping device or even the entirety of the tissue gripping device (e.g., the entire device may be sprayed, dipped, or otherwise coated in a polymer coating that forms the cover). Alternatively, some embodiments may include a cover (such as some of the covers 350 illustrated in FIGS. 11A-11C) positioned over less of the tissue gripping device such that other portions of the tissue gripping member and/or arm are exposed (e.g., inner and/or outer portions).

In some embodiments, one or more tissue gripping members may be coupled to an arm of the flexible member using suture lines as discussed with respect to FIGS. 10A-10C in addition to being held in place using a cover as discussed with respect to FIGS. 11A-11C. For example, one or more suture loops and/or suture fastening structures may be used to fasten one or more tissue gripping members to the flexible member. Afterwards (or alternatively before or at the same time), a polymer coating may be applied to form a cover surrounding at least a portion of the tissue gripping member and at least a portion of the coinciding arm.

IV. Methods of Manufacture

Embodiments of tissue gripping devices of the present disclosure may be manufactured by forming a flexible member from a shape-memory material (such as nitinol). Forming the flexible member may be accomplished by cutting a pattern shape from of shape-memory material sheet stock (or alternatively strip or band stock or other forms of stock). Various features (e.g., furcated sections, holes, etc.) may optionally be formed in the flexible member either during or after the initial formation of the flexible element from the stock material. This may be accomplished using any suitable subtractive manufacturing process such as drilling, lathing, die stamping, cutting, or the like. In some embodiments, other features may be added using an additive manufacturing process. In other embodiments, no additional features or elements are formed through any subtractive or additive manufacturing process.

In some embodiments, the flexible member may be further processed through a shape setting process. For example, one or more bend features may be formed in the flexible member by subjecting the flexible member to a heated shape setting process in order to set the shape of the bend in the shape-memory material of the flexible member.

In some embodiments, one or more tissue gripping members are formed separate from the flexible member. Forming the tissue gripping member(s) may be accomplished through a cutting and/or progressive die stamping process of a material having a suitable machinability profile for such a manufacturing process. For example, the material from which the one or more tissue gripping members are formed may be obtained by cutting and/or die stamping a shape from sheet stock (or alternatively strip or band stock or other forms of stock). For example, stock material may be stainless steel or a cobalt-chromium alloy, such as a cobalt-chromium-nickel alloy or a cobalt-chromium-nickel-iron-molybdenum-manganese alloy. In preferred embodiments, the tissue gripping member is formed from Elgiloy®. Various features (e.g., holes, frictional elements, slotted recesses, etc.) may be formed on the tissue gripping member as it is formed from the stock material.

In some embodiments, the tissue gripping member may be further manufactured through a single or progressive die stamping process. For example, the tissue gripping member may be subjected to a progressive die stamping process in order to form and/or further define a variety of features on the tissue gripping member, such as a plurality of raised barbs and slotted recesses.

In some embodiments, after formation of the flexible member and the tissue gripping member, the tissue gripping member is attached to the flexible member by coupling a mating surface of the tissue gripping member (e.g., mating surface 124 of the embodiment of FIGS. 9A-9C) to an attachment surface (e.g., attachment surface 134 of the embodiment of FIGS. 9A-9C) of the flexible member. The tissue gripping member may then be further secured to the flexible member.

For example, one or more suture lines may be wrapped or threaded around a portion of the tissue gripping member and a portion of the flexible member (e.g., an arm portion such as arm 206 of the embodiment of FIGS. 10A-10C) as illustrated in the exemplary embodiment of FIGS. 10A-10C. The suture lines may be formed into loops or may be threaded or wrapped around the tissue gripping member and the arm (or other portion of the flexible member) before being tightened and/or tied off in order to secure the tissue gripping member to the flexible member.

In some embodiments, the tissue gripping member and/or the flexible member may include holes, and the one or more suture lines may be passed through one or more of the holes in order to fasten or further secure the tissue gripping member to the flexible member. For example, as shown by the embodiment illustrated in FIGS. 10A-10C, the tissue gripping member may have a plurality of holes, with each hole configured to correspond to a hole on an arm of the flexible member when the tissue gripping member is properly positioned near or against the arm of the flexible member. One or more suture lines may pass through one or more pairs of corresponding holes as it is laced, wrapped, looped, or threaded around the tissue gripping member and the arm.

In some embodiments, one or more suture lines may also be passed through or lodged within a slotted recess of the tissue gripping member as it is laced, wrapped, looped, or threaded around the tissue gripping member and the arm. In such embodiments, the slotted recesses may further aid in securing the suture line in place and/or in preventing loosening, slippage or other unwanted movement of the suture line.

Additionally, or alternatively, the tissue gripping member may be secured to or further secured to the flexible member by adding a cover to the tissue gripping device that inserts over the arm of the flexible member and over the tissue gripping member (or portions of such) in order to hold the tissue gripping member in place against the flexible member.

For example, in some embodiments (such as in the embodiment illustrated in FIGS. 11A-11C), the cover may be a polymer material coated onto or otherwise applied to the tissue gripping device (or portions thereof). The polymer coating may then be allowed to set, cure, or otherwise form into a cover that holds the tissue gripping member in place against the arm of the flexible member. Additionally, or alternatively, the polymer coating may act as an adhesive, and may be applied to the mating surface and/or attachment surface to adhere the surfaces together.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A gripping assembly for a fixation device, the gripping assembly comprising:
   a flexible member comprising an arm having an attachment surface and at least one opening defined therein; and
   a tissue gripping member comprising:

a mating surface configured to engage the attachment surface of the arm, and a tissue gripping surface configured to engage tissue of a native heart valve leaflet, the tissue gripping member further comprising a plurality of barbs configured to resist movement of tissue relative the tissue gripping surface, wherein the tissue gripping member has at least one opening defined therein, and the tissue gripping member is attached to the arm by a suture extending through the at least one opening of the tissue gripping member and the at least one opening of the arm, and wherein the tissue gripping member has a flexibility different than a flexibility of the flexible member.

2. The gripping assembly of claim 1, wherein the flexible member is more flexible than the tissue gripping member.

3. The gripping assembly of claim 1, wherein the flexible member is made of nitinol.

4. The gripping assembly of claim 1, wherein the flexible member is made of a first material and the tissue gripping member is made of a second material, wherein the first material is different from the second material.

5. The gripping assembly of claim 4, wherein the first material is more flexible than the second material.

6. The gripping assembly of claim 1, wherein the tissue gripping member is made of a material selected from the group consisting of cobalt-chromium alloy, cobalt-chromium-nickel alloy, cobalt-chromium-nickel-iron-molybdenum-manganese alloy, stainless steel, and Elgiloy.

7. The gripping assembly of claim 1, wherein the plurality of barbs are disposed along side edges of the tissue gripping member, the tissue gripping member further having a plurality of slotted recesses defined therein along the side edges adjacent the plurality of barbs.

8. The gripping assembly of claim 1, wherein the flexible member further comprises a cover surrounding at least a portion of the arm.

9. The gripping assembly of claim 1, wherein the tissue gripping member further comprises a cover.

10. The gripping assembly of claim 1, wherein the tissue gripping member is further attached to the arm by a weld or solder.

11. The gripping assembly of claim 1, wherein the arm comprises at least one bend feature made of a shape-memory material and configured to enable movement of the arm.

12. The gripping assembly of claim 1, wherein the tissue gripping surface further includes a hole for coupling of an actuator line.

* * * * *